(12) United States Patent
Lennox et al.

(10) Patent No.: US 6,962,600 B2
(45) Date of Patent: Nov. 8, 2005

(54) METHOD AND APPARATUS FOR REDUCING BODY TEMPERATURE OF A SUBJECT

(75) Inventors: Charles D. Lennox, Hudson, NH (US); Helen Maslocka, Watertown, MA (US)

(73) Assignee: MedCool, Inc., Wellesley, MA (US)

( * ) Notice: Subject to any disclaimer, the term of this patent is extended or adjusted under 35 U.S.C. 154(b) by 0 days.

(21) Appl. No.: 10/903,469

(22) Filed: Jul. 30, 2004

(65) Prior Publication Data

US 2005/0107855 A1 May 19, 2005

Related U.S. Application Data

(60) Provisional application No. 60/492,368, filed on Aug. 4, 2003.

(51) Int. Cl.[7] .................................................. A61F 7/00
(52) U.S. Cl. .................. 607/104; 607/108; 607/112
(58) Field of Search ..................... 607/96, 104–112, 607/114

(56) References Cited

U.S. PATENT DOCUMENTS

| 2,416,788 | A | 3/1947 | Andrews ........................ 34/99 |
| 3,348,236 | A | 10/1967 | Copeland ........................... 2/2 |
| 3,587,577 | A | 6/1971 | Solyanka et al. ........... 128/254 |
| 3,610,323 | A | 10/1971 | Troyer ......................... 165/46 |
| 3,648,289 | A | 3/1972 | Moreland .................... 2/2.1 R |
| 3,908,655 | A | 9/1975 | Lund ........................... 128/256 |
| 4,172,495 | A | 10/1979 | Zebuhr et al. ................ 165/46 |
| 4,286,439 | A | 9/1981 | Pasternack ................. 62/259.3 |
| 4,390,997 | A | 7/1983 | Hinz et al. ........................ 2/81 |
| 4,425,916 | A | 1/1984 | Bowen ........................ 128/403 |
| 4,566,455 | A | 1/1986 | Kramer ....................... 128/380 |
| 4,572,188 | A | 2/1986 | Augustine et al. .......... 128/380 |
| 4,691,762 | A | 9/1987 | Elkins et al. .................. 165/46 |
| 4,738,119 | A | 4/1988 | Zafred ....................... 62/259.3 |
| 4,753,242 | A | 6/1988 | Saggers ....................... 128/380 |
| 4,781,193 | A | 11/1988 | Pagden ....................... 128/402 |
| 4,869,250 | A | 9/1989 | Bitterly ....................... 128/400 |

(Continued)

FOREIGN PATENT DOCUMENTS

| JP | 05220186 A | 8/1993 | ............. A61F/7/00 |
| JP | 05220187 A | 8/1993 | ............. A61F/7/00 |

OTHER PUBLICATIONS

Tooley, et al., "Head Cooling with Mild Systemic Hypothermia in Anesthetized Piglets is Neuroprotective", Annals of Neurology, vol. 53, No. 1, pp. 65–72, Jan. 2003.

Tooley, et al., "Significant Selective Head Cooling can be Maintained Long–Term After Global Hypoxia Ischemia in Newborn Piglets", Pediatrics, vol. 109, No. 4, pp. 643–649, Apr. 2002.

Hachimi–Idrissi, et al., "Mild Hypothermia Induced by a Helmet Device: A Clinical Feasibility Study", Resuscitation 51:275–281 (2001).

*Primary Examiner*—Roy D. Gibson
(74) *Attorney, Agent, or Firm*—Thomas J. Engellenner; Jeffrey J. Duquette; Nutter McClennen & Fish LLP

(57) ABSTRACT

A cooling system includes a pressurized liquid refrigerant source having a liquid refrigerant and a cooling garment coupled to the liquid refrigerant source. The cooling garment defines chambers containing a heat transfer fluid. During operation, a user places the cooling garment in thermal communication with a body portion of a subject. As the cooling garment receives the liquid refrigerant from the pressurized source, the liquid refrigerant thermally contacts the heat transfer fluid and evaporates, thereby reducing the temperature of the heat transfer fluid. The heat transfer fluid, in turn, reduces the temperature of the body portion in thermal communication with the cooling garment. The heat transfer fluid acts to substantially evenly distribute cooling, as provided by the evaporation of the liquid refrigerant, to the body portion contacting the cooling garment to minimize localized "cold spots" within the chamber.

21 Claims, 10 Drawing Sheets

U.S. PATENT DOCUMENTS

| | | | |
|---|---|---|---|
| 4,920,963 A | 5/1990 | Brader | 128/402 |
| 4,998,415 A | 3/1991 | Larsen | 62/231 |
| 5,062,424 A | 11/1991 | Hooker | 128/379 |
| 5,292,347 A | 3/1994 | Pompei | 607/104 |
| 5,342,411 A | 8/1994 | Maxted et al. | 607/107 |
| 5,415,222 A * | 5/1995 | Colvin et al. | 165/46 |
| 5,438,707 A | 8/1995 | Horn | 2/69 |
| 5,562,604 A | 10/1996 | Yablon et al. | 601/148 |
| 5,603,728 A | 2/1997 | Pachys | 607/110 |
| 5,609,619 A | 3/1997 | Pompei | 607/104 |
| 5,643,336 A | 7/1997 | Lopez-Claros | 607/104 |
| 5,871,526 A | 2/1999 | Gibbs et al. | 607/104 |
| 5,913,885 A | 6/1999 | Klatz et al. | 607/104 |
| 6,030,412 A | 2/2000 | Klatz et al. | 607/104 |
| 6,050,099 A | 4/2000 | Lopa et al. | 62/259.3 |
| 6,086,609 A | 7/2000 | Buckley | 607/104 |
| 6,128,784 A | 10/2000 | Frank | 2/102 |
| 6,156,059 A | 12/2000 | Olofsson | 607/109 |
| 6,178,562 B1 | 1/2001 | Elkins | 2/458 |
| 6,245,094 B1 | 6/2001 | Pompei | 607/104 |
| 6,245,096 B1 | 6/2001 | Tomic-Edgar et al. | 607/107 |
| 6,277,143 B1 | 8/2001 | Klatz et al. | 607/104 |
| 6,312,453 B1 | 11/2001 | Stefanile et al. | 607/109 |
| 6,375,674 B1 | 4/2002 | Carson | 607/104 |
| 6,461,379 B1 | 10/2002 | Carson et al. | 607/104 |
| 6,581,400 B2 | 6/2003 | Augustine et al. | 62/259.3 |
| 2002/0161419 A1 | 10/2002 | Carson et al. | 607/104 |

* cited by examiner

METHOD AND APPARATUS FOR REDUCING BODY TEMPERATURE OF A SUBJECT

RELATED APPLICATIONS

This application claims benefit of U.S. Provisional Application Ser. No. 60/492,368 filed Aug. 4, 2003, the entire teachings of which are incorporated herein by reference.

BACKGROUND

Those working in a hot environment are subject to discomfort, heat exhaustion or heat stroke. Discomfort due to heat greatly reduces worker productivity. Heat exhaustion precludes a continuation of work, and requires immediate medical attention. Heat stroke is often lethal. Workers that wear protective garments in a hot environment are particularly vulnerable to discomfort, heat exhaustion, and heat stroke.

Soldiers are required to where a chemical protection suite if a threat of chemical or biological attack is present. In a hot environment, such as the desert during summer, wearing a chemical protection suit is very uncomfortable, and can quickly lead to heat exhaustion. Firefighters, wearing fire protection suits are also subject to discomfort and heat exhaustion. Many foundry and construction workers also are required to wear protective suites and work in hot environments.

Induction of systemic hypothermia (e.g., a hypothermic state) in a patient may minimize ischemic injury when the patient suffers from a stroke, cardiac arrest, heart attack, trauma, surgery, or other injury or insult to the body resulting in ischemia. For example, in the case where the patient suffers a heart attack, the effectiveness of hypothermia is a function of the depth (e.g., within a temperature range between approximately 30° C. and 35° C. for example) and duration of the hypothermic state as applied to the heart. The effectiveness of the hypothermia is also a function of the amount of time that elapses between the original insult (e.g., heart attack) and achievement of protective levels of hypothermia. Also, for trauma and stroke patients, hypothermia aids in controlling swelling of the patient's brain. Furthermore, surgeons typically use hypothermia during brain and other invasive surgeries to protect the brain from surgical interruptions in blood flow.

It has long been known that hypothermia (body temperature lower than normal) is neuroprotective. Hypothermia has a positive affect on all known mechanisms that lead to secondary brain injury. Hypothermia is routinely used during brain and other invasive surgeries to protect the brain from surgical interruptions in blood flow. Hypothermia has also been shown to be effective in controlling swelling of the brain in trauma and stroke patients.

Systemic hypothermia has historically been applied, such as by immersion of the patient's body in a cool bath, where the depth and duration of hypothermia is limited by the patient's ability to tolerate the therapy. Currently, there are several conventional systemic hypothermia systems available. Such conventional systems include blankets or pads where cooled water is circulated through channels in the walls of the blanket or pad and the patient's body contacts the walls of the blanket.

Attempts have been also made to induce hypothermia in a patient by local cooling the surface of the patient's head. For example, Huyghens et al. (Resuscitation 51 (2001) 275–281) demonstrated that it is feasible to remove a sufficient amount of heat through the scalp to induce hypothermia in an adult using a simple cooling cap.

In another example, a conventional head-cooling device involves a head cap with a gel substance contained within the walls of the cap. Prior to use, for example, a user (e.g., medical technician) places the head-cooling device in a freezer to reduce the temperature of the gel within the cap. During operation, the user fits the reduced-temperature cap to the head of a patient. The gel within the walls of the cap absorbs heat from the head, thereby cooling the head of the patient.

Other conventional devices induce systemic hypothermia in a patient by providing contact between a tissue region of interest and a cooling fluid. For example, one conventional device includes a flexible hood having multiple ribs or studs disposed on the inner surface of the hood. When a user places the hood on a head of a patient, the ribs or studs contact the head and maintain a fluid circulation space between the head and the hood and an edge, defined by the hood, contacts the patient's skin. A negative pressure source draws a cooling fluid through the flexible hood, under negative pressure, to cause the fluid to contact the scalp of the patient and draw heat away from (e.g., cool) the scalp. Furthermore, application of the negative pressure seals the edges of the hood against the skin of the patient (e.g., a region substantially free of hair).

Additionally, intravascular catheter based systems directly cool the blood of the patient with an indwelling heat exchanger mounted on the end of a catheter that resides in the central venous system during use.

SUMMARY

Conventional techniques for providing cooling a patient or providing systemic hypothermia to a patient suffer from a variety of deficiencies.

As indicated above, systemic hypothermia reduces ischemic injury from stroke, cardiac arrest, heart attack, trauma, and surgery. However, there are several drawbacks to the approaches described above. For example, application of systemic hypothermia can take several hours to lower a patient's body to therapeutic temperatures. Such a time period delays achieving therapeutic temperatures within the patient and, therefore, allows the progression of irreversible injury to the brain or heart. In another drawback to known systemic hypothermia systems, systemic hypothermia cannot be initiated until after the patient has been admitted to the hospital.

As indicated above, attempts have been made to induce systemic hypothermia by using head-cooling devices to cool the surface of the head, such as a head cap with a gel substance contained within the walls of the cap. For example, during operation, the user fits the reduced-temperature cap to the head of a patient. The gel within the walls of the cap absorbs heat from the head, thereby cooling the head of the patient. Reports from clinical trials using such devices indicate, however, that while these devices induce systemic hypothermia, such induction is performed at a relatively slow rate. A significant problem is that hair, especially dry hair, is a very effective insulator. There is significant variation from patient to patient in the thickness of hair on the head and its distribution on the head. A device that does not address the insulating effect of hair, and its variability among patients will be ineffective in rapidly inducing systemic hypothermia in a patient.

A second significant deficiency with conventional head-cooling devices relates to the separation of the cooling medium (e.g., gel or circulating water) from the head by a material forming the device. Typically, head-cooling devices are made of plastic or woven material, both of which are highly insulative and greatly reduce the amount of heat that is transferred from the head into the cooling medium.

Also as indicated above, conventional head-cooling devices include a flexible hood placed on the head of a patient. A cooling fluid is drawn through the flexible hood under negative pressure to contact the scalp of the patient and draw heat away from (e.g., cool) the patient's scalp. Because the flexible hood, however, relies on a negative pressure to draw the cooling fluid within a region between the scalp and the hood apparatus, a large number of regularly spaced ribs or studs are required to form fluid channels between the scalp and the apparatus. Furthermore, application of the negative pressure seals the edges of the hood against the skin of the tissue region. However, such sealing is ineffective when the edges are positioned over hair, such as hair protruding from a patient scalp. In the case where the edges contact the hair of a patient's scalp, the hair minimizes the seal between the hood and the patient, thereby allowing leakage of the cooling fluid from the hood apparatus.

Additionally, the aforementioned intravascular catheter based systems provides relatively rapid cooling to a subject. However, use of such a device requires advanced imaging equipment to insert the catheter into the patient, and advanced surgical skill, precluding use in the emergent care setting.

Furthermore, the aforementioned conventional cooling modalities to cool a subject working in a hot environment suffer from a variety of deficiencies.

For example, the conventional head-cooling devices include a closed loop system comprising a console, which contains a pump, a reservoir of water, an electrical power source, a means of cooling the water, and a hood and umbilical having at least two fluid tubes. The use of the conventional head-cooling devices that rely on the closed loop circulation of water with a console to maintain worker comfort in a hot environment is not practical. Using a head cap with a gel substance contained within the walls of the cap to maintain worker comfort in a hot environment is also not practical. Conventional gel cap technology requires that the gel-filled head-cooling device be stored in a freezer until immediately prior to use. As such, this requirement also precludes use in most work places.

By contrast, embodiments of the present invention significantly overcome such deficiencies and provide techniques for reducing temperature in a subject. A cooling system includes a pressurized liquid refrigerant source having a liquid refrigerant and a cooling garment coupled to the liquid refrigerant source. The cooling garment defines chambers containing a heat transfer fluid. During operation, a user places the cooling garment in thermal communication with a body portion of a subject. As the cooling garment receives the liquid refrigerant from the pressurized source, the liquid refrigerant thermally contacts the heat transfer fluid and evaporates, thereby reducing the temperature of the heat transfer fluid. The heat transfer fluid, in turn, reduces the temperature of the body portion in thermal communication with the cooling garment. The heat transfer fluid acts to substantially evenly distribute cooling, as provided by the evaporation of the liquid refrigerant, to the body portion contacting the cooling garment to minimize localized "cold spots" within the chamber. In one arrangement, the heat transfer fluid has a freezing point configured such that the surface of the cooling garment (e.g., the surface of a wall forming the chamber) in thermal communication with the body portion and in thermal communication with the heat transfer fluid maintains a temperature above approximately zero degrees centigrade (0° C.). In such an arrangement, with the surface of the cooling garment in contact with the body portion at a temperature above approximately 0° C., the heat transfer fluid provides heat transfer with the body portion (e.g., a maximal level of heat transfer) while minimizing injury, such as frostbite) to the body portion.

Nowhere in the art is a method or apparatus for maintaining worker comfort in a hot environment described using a cooling cap, an umbilical having a single liquid conduit, and a cooling source connected to the cooling cap by the umbilical.

Nowhere in the art is a method or apparatus for maintaining worker comfort in a hot environment described using a helmet with a liner, a removable umbilical having a single liquid conduit, and a cooling source that may be removably connected to the helmet by the umbilical; whereby the liner normally provides padding for comfort and fit, and in the instance where the worker becomes uncomfortable due to environmental heat, the helmet can be connected to the cooling source with the umbilical, where the liner then functions to cool the worker to obtain or maintain comfort.

Nowhere in the art is a method or apparatus for maintaining worker comfort in a hot environment described using a cooling cap, an umbilical having a single liquid conduit, and a cooling source connected to the cooling cap by the umbilical; whereby the cooling source consists of a container of passively pressurized liquid, and an umbilical connection means.

Nowhere in the art is a method or apparatus for maintaining worker comfort in a hot environment described using a cooling cap, an umbilical having a single liquid conduit, and a cooling source having passively pressurized cooling liquid connected to the cooling cap by the umbilical; whereby the cooling cap having a liquid flow control valve, a gas pressure control valve, at least one liquid evaporator, and a space within the walls of the cap containing convective heat transfer liquid.

Nowhere in the art is a method or apparatus for maintaining worker comfort in a hot environment described using a cooling cap, an umbilical having a single liquid conduit, and a cooling source having a passively pressurized cooling liquid connected to the cooling cap by the umbilical; whereby cooling liquid enters the cooling cap under pressure and is evaporated into a gaseous state within the cooling cap, where evaporation of the liquid provides a cooling means, and where optionally the pressure of the resulting gas is regulated within the cooling cap to provide a means for expanding the walls of the cooling cap to provide a snug fit with the workers head.

Nowhere in the art is a method or apparatus for maintaining worker comfort in a hot environment described using a cooling cap, an umbilical having a single liquid conduit, and alternately an umbilical having a liquid conduit and a gas conduit, and a cooling source connectable to the cooling cap by the umbilical; whereby the cooling source may consist of a container of liquid under pressure and a connection means for the single conduit umbilical, or may include a refrigeration unit with a connection means for the two conduit umbilical.

Nowhere in the art is a method or apparatus for maintaining worker comfort in a hot environment described using a cooling cap, an umbilical having a single liquid conduit, and a cooling source including a passively pressurized cooling liquid connected to the cooling cap by the umbilical; whereby heat transfer between the workers head and the cooling cap is enhanced by means of a heat transfer gel or liquid in the space between the workers head and the cooling cap.

Nowhere in the art is a method or apparatus for maintaining worker comfort in a hot environment described using a cooling cap, an umbilical having a single liquid conduit, a cooling source including a passively pressurized cooling liquid connected to the cooling cap by the umbilical, and heat transfer liquid or gel; whereby the liquid or gel having a suspension of metal power.

Nowhere in the art is a method or apparatus for maintaining worker comfort in a hot environment described using a cooling cap, an umbilical having a single liquid conduit, a cooling source including a passively pressurized cooling liquid connected to the cooling cap by the umbilical, and heat transfer liquid or gel; whereby the liquid or gel including a topical anesthetic.

Nowhere described in the art is a method and/or apparatus for inducing hypothermia to a therapeutic level in a patient using, a cooling cap, an umbilical having a single liquid conduit, a cooling source having a container of passively pressurized liquid and an umbilical connection means; whereby the cooling cap is connected to the cooling source by the umbilical.

Nowhere in the art is an integrated apparatus for resuscitation described using a defibrillation means, a cooling cap, an umbilical having a single liquid conduit, a cooling source having a container of passively pressurized liquid and an umbilical connection means; whereby the cooling cap is connected to the cooling source by the umbilical.

Nowhere in the art is a portable resuscitation apparatus described having a console that is small enough, and light enough to be hand carried to and alongside a patient having a defibrillator and a means for rapidly lowering patient body temperature to a temperature between 30 and 37 degrees centigrade; whereby the body temperature lowering means does not require electrical energy for operation.

Therefore, embodiments of the invention to provide a method, and apparatus for preventing discomfort, heat exhaustion, or heat stroke in individuals working in a hot environment.

In accordance with another embodiment of the invention is an apparatus for rapidly obtaining an optimal body temperature in a patient in the emergent care setting in which resuscitation is clinically indicated.

In accordance with another embodiment of the invention is an apparatus for preventing discomfort, heat exhaustion, or heat stroke in an individual working in a hot environment whereby the apparatus does not interfere with the work of the individual in any significant manner.

In accordance with another embodiment of the invention, is an apparatus that provides for rapid obtainment of an optimal body temperature in a patient undergoing resuscitation that does not interfere in any significant manner with resuscitation by widely accepted resuscitation practices.

In accordance with another embodiment of the invention is an apparatus for preventing discomfort, heat exhaustion, or heat stroke in an individual working in a hot environment whereby the apparatus does not interfere with the work of the individual in any significant manner, having a cooling cap, an umbilical having a single liquid conduit, and a cooling source having a passively pressurized cooling liquid connected to the cooling cap by the umbilical.

In accordance with another embodiment of the invention, is an apparatus that provides for rapid obtainment of an optimal body temperature in a patient undergoing resuscitation that does not interfere in any significant manner with resuscitation by widely accepted resuscitation practices, having a cooling cap, an umbilical having a single liquid conduit, and a cooling source having a passively pressurized cooling liquid connected to the cooling cap by the umbilical.

In accordance with another embodiment of the invention is an apparatus for preventing discomfort, heat exhaustion, or heat stroke in an individual working in a hot environment where the apparatus does not interfere with the work of the individual in any significant manner, having a cooling cap, an umbilical having a single liquid conduit, and a cooling source connected to the cooling cap by the umbilical, whereby the cooling source consists of a disposable or reusable container of passively pressurized cooling liquid, and an umbilical connection means.

In accordance with another embodiment of the invention, is an apparatus that provides for rapid obtainment of an optimal body temperature in a patient undergoing resuscitation that does not interfere in any significant manner with resuscitation by widely accepted resuscitation practices, having a cooling cap, an umbilical having a single liquid conduit, and a cooling source connected to the cooling cap by the umbilical, whereby the cooling source consists of a disposable, reusable, or refillable container of passively pressurized cooling liquid, and an umbilical connection means.

In accordance with another embodiment of the invention is an apparatus for preventing discomfort, heat exhaustion, or heat stroke in an individual working in a hot environment whereby the apparatus does not interfere with the work of the individual in any significant manner, having a cooling cap, an umbilical having a single liquid conduit, and a cooling source having passively pressurized cooling liquid connected to the cooling cap by the umbilical, whereby the cooling cap has a cooling liquid flow control valve, a gas pressure control valve, at least one liquid evaporator, and a space within the walls of the cap containing convective heat transfer liquid, and a means for the individual to adjust the flow rate of the cooling liquid.

In accordance with another embodiment of the invention, is an apparatus that provides for rapid obtainment of an optimal body temperature in a patient undergoing resuscitation that does not interfere in any significant manner with resuscitation by widely accepted resuscitation practices, having a cooling cap, an umbilical having a single liquid conduit, and a cooling source having passively pressurized cooling liquid connected to the cooling cap by the umbilical, whereby the cooling cap has a cooling liquid flow control valve, a gas pressure control valve, at least one liquid evaporator, and a space within the walls of the cap containing convective heat transfer liquid, and optionally a means for the caregiver to adjust the flow rate of the cooling liquid.

In accordance with another embodiment of the invention is an apparatus for preventing discomfort, heat exhaustion, or heat stroke in an individual working in a hot environment whereby the apparatus does not interfere with the work of the individual in any significant manner, having a cooling cap, an umbilical having a single liquid conduit, and a cooling source having passively pressurized cooling liquid connected to the cooling cap by the umbilical, whereby heat transfer between the workers head and the cooling cap is enhanced by means of a heat transfer gel or liquid in the space between the workers head and the cooling cap.

In accordance with another embodiment of the invention, is an apparatus that provides for rapid obtainment of an optimal body temperature in a patient undergoing resuscitation that does not interfere in any significant manner with resuscitation by widely accepted resuscitation practices, having a cooling cap, an umbilical having a single liquid conduit, and a cooling source having passively pressurized cooling liquid connected to the cooling cap by the umbilical, whereby heat transfer between the workers head and the cooling cap is enhanced by means of a heat transfer gel or liquid in the space between the workers head and the cooling cap.

In accordance with another embodiment of the invention is an apparatus for preventing discomfort, heat exhaustion, or heat stroke in an individual working in a hot environment whereby the apparatus does not interfere with the work of the individual in any significant manner, having a cooling cap, an umbilical having a single liquid conduit, a cooling source having a passively pressurized cooling liquid connected to the cooling cap by the umbilical, and heat transfer liquid or gel; whereby the heat transfer liquid or gel includes a suspension of metal powder.

In accordance with another embodiment of the invention, is an apparatus that provides for rapid obtainment of an optimal body temperature in a patient undergoing resuscitation that does not interfere in any significant manner with resuscitation by widely accepted resuscitation practices, having a cooling cap, an umbilical having a single liquid conduit, a cooling source having a passively pressurized cooling liquid connected to the cooling cap by the umbilical, and heat transfer liquid or gel; whereby the heat transfer liquid or gel having a suspension of metal power.

In accordance with another embodiment of the invention is an apparatus for preventing discomfort, heat exhaustion, or heat stroke in an individual working in a hot environment whereby the apparatus does not interfere with the work of the individual in any significant manner, having a cooling cap, an umbilical having a single liquid conduit, a cooling source having a passively pressurized cooling liquid connected to the cooling cap by the umbilical, and heat transfer liquid or gel; whereby the heat transfer liquid or gel includes a topical anesthetic.

In accordance with another embodiment of the invention, is an apparatus that provides for rapid obtainment of an optimal body temperature in a patient undergoing resuscitation that does not interfere in any significant manner with resuscitation by widely accepted resuscitation practices, having a cooling cap, an umbilical having a single liquid conduit, a cooling source having a passively pressurized cooling liquid connected to the cooling cap by the umbilical, and heat transfer liquid or gel; whereby the heat transfer liquid or gel includes a topical anesthetic.

In accordance with another embodiment of the invention is an apparatus for preventing discomfort, heat exhaustion, or heat stroke in an individual working in a hot environment whereby the apparatus does not interfere with the work of the individual in any significant manner, having a cooling garment, an umbilical having a single liquid conduit, a cooling source connected to the cooling garment by the umbilical.

In accordance with another embodiment of the invention, is an apparatus that provides for rapid obtainment of an optimal body temperature in a patient undergoing resuscitation that does not interfere in any significant manner with resuscitation by widely accepted resuscitation practices, having a cooling cap, one or more additional cooling garment(s), one or more umbilicals (e.g., connectors) having a single liquid conduit, a cooling source having a passively pressurized cooling liquid connected to the cooling cap and additional cooling garment(s) by the umbilical(s).

In accordance with another embodiment of the invention, is an apparatus for rapidly obtaining an optimal body temperature in a patient in the emergency care setting that is small enough and light enough to be hand carried to a stricken patient, and to then be hand carried and operated in close proximity to the patient during patient transport and while the patient is in the care of the emergency department of a hospital having a cooling cap, an umbilical having a single liquid conduit, and a cooling source having a passively pressurized cooling liquid connected to the cooling cap by the umbilical, whereby the cooling cap has a cooling liquid flow control valve, a gas pressure control valve, at least one liquid evaporator, and a space within the walls of the cap containing convective heat transfer liquid, and optionally a means for the caregiver to adjust the flow rate of the liquid.

In accordance with another embodiment of the invention, is an apparatus for rapidly obtaining an optimal body temperature in a patient in the emergency care setting that is small enough and light enough to be hand carried to a stricken patient, and to then be hand carried and operated in close proximity to the patient during patient transport and while the patient is in the care of the emergency department of a hospital having one or more cooling garment(s), an umbilical(s) having a single liquid conduit, and a cooling source having a passively pressurized cooling liquid connected to the cooling garment(s) by the umbilical(s), whereby the cooling garment(s) has a cooling liquid flow control valve, a gas pressure control valve, at least one liquid evaporator, and a space within the walls of the cooling garment(s) containing convective heat transfer liquid and optionally a means for the caregiver to adjust the flow rate of the cooling liquid.

In accordance with another embodiment of the invention is a small portable resuscitation apparatus having a defibrillation means, a cooling cap, an umbilical having a single liquid conduit, a cooling source having a container of passively pressurized liquid and an umbilical connection means; whereby the cooling cap is connected to the cooling source by the umbilical.

In accordance with another embodiment of the invention is a small portable resuscitation apparatus having a defibrillation, device, a chest compression apparatus, an intravenous fluid infusion device, a cooling cap, an umbilical having a single liquid conduit, a cooling source having a container of passively pressurized liquid and an umbilical connection means; whereby the cooling cap is connected to the cooling source by the umbilical, and whereby the cooling cap has a liquid flow control valve, a gas pressure control valve, at least one liquid evaporator, and a space within the walls of the cap containing convective heat transfer liquid and optionally a means for the caregiver to adjust the flow rate of the cooling liquid.

In accordance with another embodiment of the invention is a small portable resuscitation apparatus having a defibrillation means, one or more cooling garment(s), one or more umbilical(s) having a single liquid conduit, a cooling source having a container of passively pressurized liquid and an umbilical connection means; whereby the cooling garment(s) is connected to the cooling source by the umbilical(s), and whereby the cooling garment(s) has a liquid flow control valve, a gas pressure control valve, at least one liquid evaporator, and a space within the walls of the cooling garment(s) containing convective heat transfer liquid and optionally a means for the caregiver to adjust the flow rate of the liquid.

In accordance with another embodiment of the invention, is a combat helmet having a bullet resistant outer shell and a cooling inner liner, whereby the cooling inner liner has a gas pressure control valve, at least one liquid evaporator, and a space within the walls of the cooling liner containing convective heat transfer liquid.

In accordance with another embodiment of the invention, is a construction helmet having a rigid and hard outer shell and a cooling inner liner, whereby the cooling inner liner has a gas pressure control valve, at least one liquid evaporator, and a space within the walls of the cooling liner containing convective heat transfer liquid.

In accordance with another embodiment of the invention, an apparatus is provided that induces hypothermia in a patient's body such that the brain of the patient is cooled to a greater degree than the rest of the patient's body, whereby the apparatus has a cooling cap, an umbilical having a single liquid conduit, a cooling source having a container of passively pressurized liquid and an umbilical connection means; whereby the cooling cap is connected to the cooling source by the umbilical.

In accordance with another embodiment of the invention, is an apparatus that effectively cools the head of a patient, thereby cooling the body of the patient, whereby the effectiveness the head cooling is not substantially affected by the thickness or distribution of the hair on the head, face, or neck of the patient, and whereby the apparatus includes a cooling cap, an umbilical having a single liquid conduit, a cooling source having a container of passively pressurized liquid, and an umbilical connection means, and heat transfer liquid or gel, whereby the cooling cap is connected to the cooling source by the umbilical, and the heat transfer liquid or gel diminishes the insulating effect of hair.

In accordance with another embodiment of the invention is a cooling cap having an umbilical, or an umbilical connection means, at least one liquid evaporator, a cooling liquid flow control valve, a gas pressure regulation valve, and a space within the walls of the cooling cap containing thermal convection heat transfer fluid.

In accordance with another embodiment of the invention, an apparatus for resuscitation is a crash cart having a means for lowering patient body temperature having a cooling cap, an umbilical having a single liquid conduit, a cooling source having a container of passively pressurized liquid, an umbilical connection means, and heat transfer liquid or gel, a means to store resuscitation medications, supplies and devices, and a means to transport the crash cart from a place of storage to a patient in need of resuscitation, whereby the cooling cap is connected to the cooling source by the umbilical, and the heat transfer liquid or gel diminishes the insulating effect of hair.

In accordance with another embodiment of the invention, is an apparatus for rapidly obtaining and then maintaining an optimal body temperature in a patient in the emergency care setting that is small enough and light enough to be hand carried to a stricken patient, and to then be hand carried and operated in close proximity to the patient during patient transport and while the patient is in the care of the emergency department of a hospital having; a small portable console that includes a passively pressurized cooling liquid source, electronic controls, an electrically actuated cooling liquid flow control valve, an electrical battery, a means for the user to set a target patient body temperature, an umbilical connection means, and a patient temperature sensor connection means, a patient temperature sensor, a cooling cap having a gas pressure control valve, at least one liquid evaporator, and a space within the walls of the cap containing convective heat transfer liquid, and an umbilical having a single liquid conduit, whereby the patient temperature sensor provides signals to the control circuit indicative of patient temperature and the control circuit adjusts the flow of cooling liquid to the cooling cap thereby providing thermostatic control of the temperature of the patient at the user set point.

In accordance with another embodiment of the invention, is an apparatus for rapidly obtaining and then maintaining an optimal body temperature in a patient in the emergency care setting that is small enough and light enough to be hand carried to a stricken patient, and to then be hand carried and operated in close proximity to the patient during patient transport and while the patient is in the care of the emergency department of a hospital having; a small portable console that includes a passively pressurized cooling liquid source, electronic controls, an electrical battery, a means for the user to set a target patient body temperature, an umbilical connection means, and a patient temperature sensor connection means, a patient temperature sensor, a cooling cap having an electrically actuated cooling liquid flow control valve, a gas pressure control valve, at least one liquid evaporator, and a space within the walls of the cap containing convective heat transfer liquid, and an umbilical having a single liquid conduit and at least one electrical conduit that electrically connects the cooling liquid flow control valve to the console, whereby the patient temperature sensor provides signals to the control circuit indicative of patient temperature and the control circuit adjusts the flow of cooling liquid to the cooling cap thereby providing thermostatic control of the temperature of the patient at the user set point.

In accordance with another embodiment of the invention, is a method of resuscitation including the steps of bringing to a stricken patient an apparatus that provides a means for lowering the patient's body temperature to a predetermined level, and then maintaining the patient's body temperature at the predetermined level for an extended period of time, where the apparatus includes a cooling cap that includes a gas pressure control valve, at least one liquid evaporator, and a space within the walls of the cap containing convective heat transfer liquid, a small portable console that includes a passively pressurized cooling liquid source, electronic controls, an electrically actuated cooling liquid flow control valve, an electrical battery, a means for the user to set a target patient body temperature, an umbilical connection means, and a patient temperature sensor connection means, and a body temperature sensor, then initiating resuscitation, then placing the cooling cap on the head of the patient, then connecting the cooling cap to the small portable console with the umbilical, then activating the small portable console, whereby activating the small portable console initiates a cool down mode of operation whereby the cool down mode of operation includes a continuous flow of cooling liquid from the small portable console to the cooling cap, then placing the body temperature sensor on the patient's body and connecting the body temperature sensor to the small portable console either before activation of the system, or after activation of the system and before the patient's body temperature reaches the predetermined temperature, then when patient's body reaches the predetermined temperature, the small portable console enters a temperature maintenance mode of operation, whereby the temperature maintenance mode of operation includes an intermittent flow of cooling liquid from the small portable console to the cooling cap, whereby the intermittence of the flow of cooling liquid is adjusted by control algorithms within the control circuits of the small portable console according to signals received from the body temperature sensor in order to maintain the patient's body temperature at the predetermined level.

In accordance with another embodiment of the invention, is a method of resuscitation including the steps of bringing to a stricken patient an apparatus that provides a means for lowering the patient's body temperature to a predetermined level, and then maintaining the patient's body temperature at the predetermined level for an extended period of time, the apparatus including a cooling cap that includes a gas pressure control valve, at least one liquid evaporator, and a space within the walls of the cap containing convective heat transfer liquid, a small portable console that comprises a passively pressurized cooling liquid source, electronic controls, an electrically actuated cooling liquid flow control valve, an electrical battery, a means for the user to set a target patient body temperature, an umbilical connection means, and a patient temperature sensor connection means, and a body temperature sensor, then initiating resuscitation, then placing the cooling cap on the head of the patient, then connecting the cooling cap to the small portable console with the umbilical, then activating the small portable console, whereby activating the small portable console initiates a cool down mode of operation whereby the cool down mode of operation includes a continuous flow of cooling liquid from the small portable console to the cooling cap, then placing the body temperature sensor on the patient's body and connecting the body temperature sensor to the small portable console either before activation of the system, or after activation of the system and before the patient's body temperature reaches the predetermined temperature, then when patient's body reaches the predetermined temperature, the small portable console enters a temperature maintenance mode of operation, whereby the temperature maintenance mode of operation includes a continuous flow of cooling liquid from the small portable console to the cooling cap, whereby the flow rate of the cooling liquid is adjusted by control algorithms within the control circuits of the small portable console according to signals received from the body temperature sensor in order to maintain the patient's body temperature at the predetermined level.

In accordance with another embodiment of the invention, is a method of resuscitation including the steps of bringing to a stricken patient an apparatus including a small battery operated console that provides a means for defibrillating the patient, and a means for rapidly lowering the body temperature of the patient where the apparatus includes a cooling cap connectable to the small portable battery operated console by an umbilical, then initiating resuscitation by defibrillating the patient with the defibrillation means provided by the small portable battery operated console, then placing the cooling cap on the head of the patient, then connecting the cooling cap to the small portable battery operated console, then activating the cooling means of the small portable battery operated console, then completing resuscitation of the patient.

In accordance with another embodiment of the invention, is a method of resuscitation including the steps of bringing to a stricken patient an apparatus having a small battery operated console that provides a means for defibrillating the patient, and a means for lowering the body temperature of the patient to a predetermined level, and then maintaining the patient's body temperature at the predetermined level for an extended period of time, the apparatus having a cooling cap connectable to the small portable battery operated console by an umbilical, then initiating resuscitation by defibrillating the patient with the defibrillation means provided by the small portable battery operated console, then placing the cooling cap on the head of the patient, then connecting the cooling cap to the small portable battery operated console, then activating the cooling means of the small portable battery operated console, then completing resuscitation of the patient.

In accordance with another embodiment of the invention, is a method of resuscitation including the steps of bringing to a stricken patient an apparatus having a small battery operated console that provides a means for defibrillating the patient, and a means for lowering the body temperature of the patient to a predetermined level by means of an internal store of passively pressurized cooling liquid, and then maintaining the patient's body temperature at the predetermined level for an extended period of time, the apparatus including a cooling cap connectable to the small portable battery operated console by an umbilical, then initiating resuscitation by defibrillating the patient with the defibrillation means provided by the small portable battery operated console, then placing the cooling cap on the head of the patient, then connecting the cooling cap to the small portable battery operated console, then activating the cooling means of the small portable battery operated console, then completing resuscitation of the patient, then deactivating the small portable battery operated console and then disconnecting the cooling cap from the small battery operated console, then connecting the cooling cap to a second console that is not battery operated, and then activating the second console thereby resuming cooling of the patient.

In accordance with another embodiment of the invention, is a method for increasing the productivity of a worker by preventing discomfort due to heat, heat exhaustion, or heat stroke, including the steps of supplying the worker with a head-cooling system, then, instructing the worker to use the head-cooling system while working, and/or while the worker is on break, whereby the head-cooling system includes a head-cooling cap, or helmet equipped with a head-cooling liner, a source of passively pressurized cooling liquid, and a means to connect the head-cooling cap, or head-cooling helmet liner to the source of pressurized cooling liquid.

In accordance with another embodiment of the invention is an apparatus for maintaining worker comfort in a hot environment including a cooling cap, an umbilical having a single liquid conduit, and a cooling source connected to the cooling cap by the umbilical; whereby liquid enters the cooling cap under pressure and is evaporated into a gaseous state within the cooling cap, where evaporation of the liquid provides a cooling means, and where the pressure of the resulting gas is regulated within the cooling cap to provide a means for expanding the walls of the cooling cap to provide a snug fit with the workers head.

In accordance with another embodiment of the invention is an apparatus for maintaining worker comfort in a hot environment including a cooling cap, an umbilical having a single liquid conduit, and alternately an umbilical having a liquid conduit and a gas conduit, and a cooling source connected to the cooling cap by the umbilical; whereby the cooling source may consist of a container of liquid under pressure and a connection means for the single conduit umbilical, or may have a refrigeration unit with a connection means for the two conduit umbilical.

In accordance with another embodiment of the invention is a liquid evaporator having metal foil walls, a liquid feed tube, and a manifold fitting.

In accordance with another embodiment of the invention is a cooling cap including a means for delivering an anesthetic agent into the scalp by iontophoresis means, such as an anode, a cathode, and a power source coupled to the anode and the cathode.

In accordance with another embodiment of the invention is a cooling cap including a cooling liquid flow control valve, a gas pressure control valve, at least one liquid evaporator, and a space within the walls of the cap containing convective heat transfer liquid.

In accordance with another embodiment of the invention is a head-cooling system including a head-cooling cap, or helmet equipped with a head-cooling liner, a source of passively pressurized cooling liquid, and a means to connect the head-cooling cap, or head-cooling helmet liner to the source of passively pressurized cooling liquid, wherein the head-cooling means includes the evaporation of the pressurized cooling liquid within the walls of the head-cooling cap or the head-cooling helmet liner.

In accordance with another embodiment of the invention is a cooling cap having a cooling liquid flow control valve, a gas pressure control valve, at least one liquid evaporator, and a space within the walls of the cap containing convective heat transfer liquid, whereby the cooling cap can be folded and stored indefinitely in a compact shape.

In accordance with another embodiment of the invention is a cooling cap having a means for receiving pressurized cooling liquid, an outer wall having a gas permeable membrane, a space within the walls of the cap containing convective heat transfer liquid, and a cooling liquid distribution means within said space.

In accordance with another embodiment of the invention is an apparatus for maintaining worker comfort in a hot environment including a helmet with a liner, a removable umbilical having a single liquid conduit, and a cooling source that may be removably connected to the helmet by the umbilical; whereby the liner normally provides padding for comfort and fit, and in the instance where the worker becomes uncomfortable due to environmental heat, the helmet can be connected to the cooling source with the umbilical, where the liner then functions to cool the worker to obtain or maintain comfort.

In accordance with another embodiment of the invention is a console having a defibrillator means, and a passively pressurized cooling liquid container means.

In accordance with another embodiment of the invention, is a kit including, a cooling cap, or a helmet, and directions for use, whereby the directions for use describe one or more of the methods for increasing worker productivity, or for resuscitation described in my patent above.

Embodiments of the present invention provide an apparatus to improve worker productivity by preventing discomfort due to heat, heat exhaustion, or heat stroke. Embodiments of the invention provide an apparatus to increase the combat effectiveness of military forces operating in a hot battlefield environment. Embodiments of the invention provide an apparatus for inducing hypothermia in patients indicated for resuscitation rapidly. Embodiments of the invention provide an apparatus for initiating hypothermia therapy in a patient indicated for resuscitation prior to arrival at the hospital. Embodiments of the invention provide an apparatus for inducing hypothermia in a patient indicated for resuscitation where protective levels of hypothermia are rapidly and preferentially induced in the brain. Embodiments of the invention provide a practical means for removing excess body heat. Embodiments of the invention provide a compact and portable resuscitation apparatus that includes a defibrillation means and a hypothermia induction means.

Embodiments of the invention provide an apparatus for rapidly inducing hypothermia in the pre-hospital setting, or upon arrival at the hospital, in a patient with cardiac arrest, acute myocardial infarction, brain trauma, embolic or hemorrhagic stroke, subarachnoid hemorrhage, or hemorrhagic shock. Embodiments of the invention provide a method of resuscitation for a patient stricken with cardiac arrest, acute myocardial infarction, brain trauma, embolic or hemorrhagic stroke, subarachnoid hemorrhage, or hemorrhagic shock. Embodiments of the invention provide a body cooling system that is compatible with emergency medical treatment practices. Embodiments of the invention provide a patient temperature control system including at least one body-cooling device that is capable of being operated by a small portable console that runs on a store of passively pressurized cooling liquid, that is also capable of being operated by a console that runs on electrical power from a wall outlet, whereby the body-cooling device may remain attached to the patient in an operational position while the body-cooling device is disconnected from one console and then connected to a second console. Other embodiments of the invention provide an integrated resuscitation apparatus, provide a method of improving worker productivity, and provide a method of increasing the combat effectiveness of military forces operating in a hot battlefield environment.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Embodiments of the present invention provide techniques for reducing temperature in a subject. A cooling system includes a pressurized liquid refrigerant source having a liquid refrigerant and a cooling garment coupled to the liquid refrigerant source. The cooling garment defines chambers containing a heat transfer fluid. During operation, a user places the cooling garment in thermal communication with a body portion of a subject. As the cooling garment receives the liquid refrigerant from the pressurized source, the liquid refrigerant thermally contacts the heat transfer fluid and evaporates, thereby reducing the temperature of the heat transfer fluid. The heat transfer fluid, in turn, reduces the temperature of the body portion in thermal communication with the cooling garment. The heat transfer fluid acts to substantially evenly distribute cooling, as provided by the evaporation of the liquid refrigerant, to the body portion contacting the cooling garment to minimize localized "cold spots" within the chamber.

In one arrangement, the heat transfer fluid has a freezing point configured such that the surface of the cooling garment (e.g., the surface of a wall forming the chamber) in thermal communication with the body portion and in thermal communication with the heat transfer fluid maintains a temperature above approximately zero degrees centigrade (0° C.). In such an arrangement, with the surface of the cooling garment in contact with the body portion at a temperature above approximately 0° C., the heat transfer fluid provides heat transfer with the body portion (e.g., a maximal level of heat transfer) while minimizing injury, such as frostbite, to the body portion.

Figure 1:
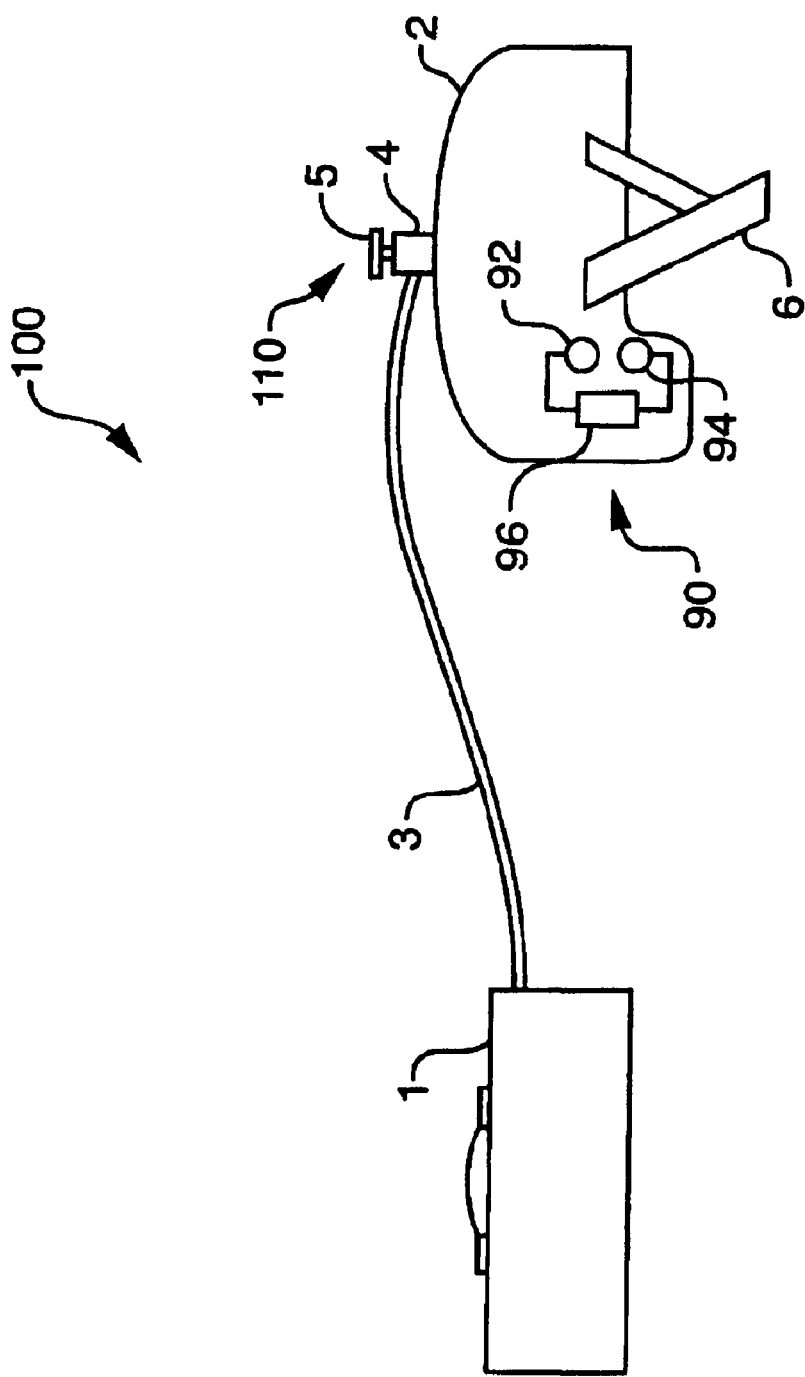
FIG. 1 illustrates a cooling system showing a cooling source, a cooling cap, and an umbilical connecting the cooling source to the cooling garment.

FIG. 1 depicts a cooling system 100 including a cooling source 1 and a cooling assembly 110. The cooling assembly 110 includes a cooling garment, such as cooling cap 2, (or helmet with cooling liner) having a fluid inlet coupled to the cooling source via umbilical 3. Cooling cap 2 includes control valve assembly 4, and cooling control knob 5. Umbilical 3 consists of a single liquid conduit, and a connector or conduit to connect to cooling source 1 and control valve assembly 4 of cooling cap 2, and provides liquid communication between cooling source 1 and control valve assembly 4. Cooling source (e.g., pressurized liquid refrigerant source) 1 consists of a passively pressurized container of cooling fluid or liquid refrigerant, such as a gas held under pressure in a liquid phase, a connector or conduit to connect umbilical 3 to the container of liquid refrigerant, and optionally a carrying case (as shown). In one embodiment, the liquid refrigerant is nitrogen, however, the apparatus can be configured to operate on alternative liquid refrigerants such as argon, freon, or others. Nitrogen is preferred due to its nature as being the main component of air, and therefore does not present an environmental hazard, its high heat of vaporization (199 KJ/Kg), and the fact that it is readily available at a low cost. Liquid refrigerant is supplied to control valve assembly 4 under pressure. Control valve 4 controls the flow of liquid refrigerant into cooling cap 1, and also controls the gas pressure inside cooling cap 1. Cooling is accomplished by evaporation of the liquid refrigerant within the walls of the cooling cap, and the resulting gas is vented through control valve assembly 4 into the atmosphere. Cooling control knob (e.g., flow control valve) 5 controls the rate at which liquid refrigerant enters the cooling cap, and therefore, the cooling rate. Chinstrap 6 secures the cooling cap to the worker's or patient's head.

Figure 2:
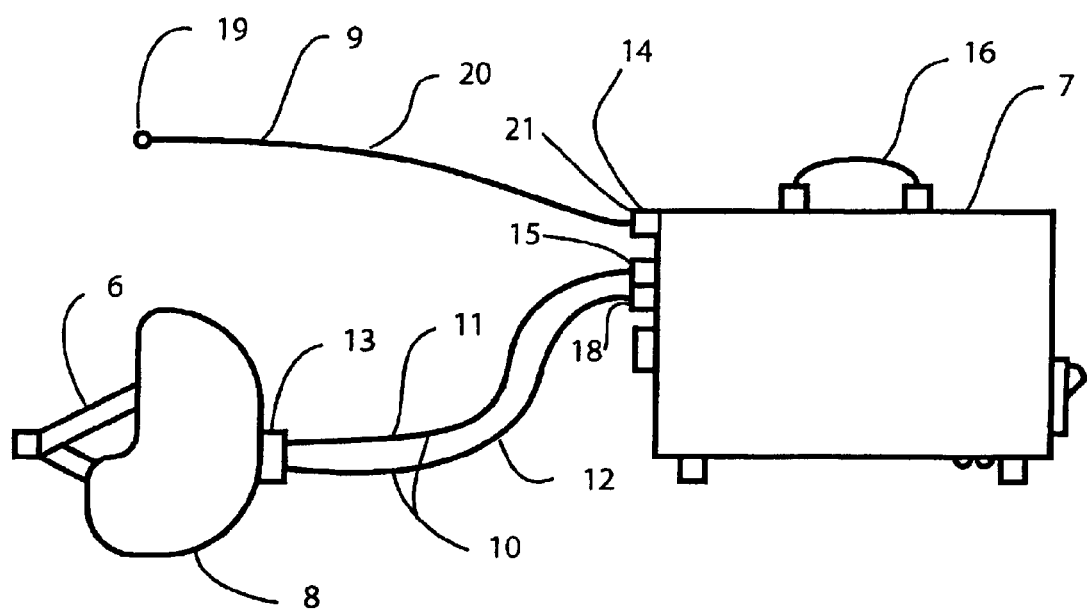
FIG. 2 depicts a resuscitation apparatus for cooling a patient having a portable console, a cooling cap, and a temperature sensor connected by umbilicals.

FIG. 2 depicts an arrangement of a resuscitation apparatus having a small portable resuscitation console 7, resuscitation-cooling cap 8, temperature sensor assembly 9, and umbilical 10. Resuscitation console 7 includes an internal container containing passively pressurized liquid refrigerant (not shown), electronic control circuits (not shown), an electrical battery (not shown), user control and display interface (not shown), temperature sensor connector 14, umbilical connector 15, carrying handle 16. Resuscitation-cooling cap 8 includes umbilical 10, electrically actuated control valve assembly 13, chinstrap 6, and cap assembly 17. Umbilical 10 includes liquid conduit 11, electrical conduit 12 and console connector 18. A physiological sensor assembly, such as a temperature sensor assembly 9, includes a physiological sensor, such as a temperature sensor 19, catheter/electrical lead 20, and console connector 21.

Figure 8:
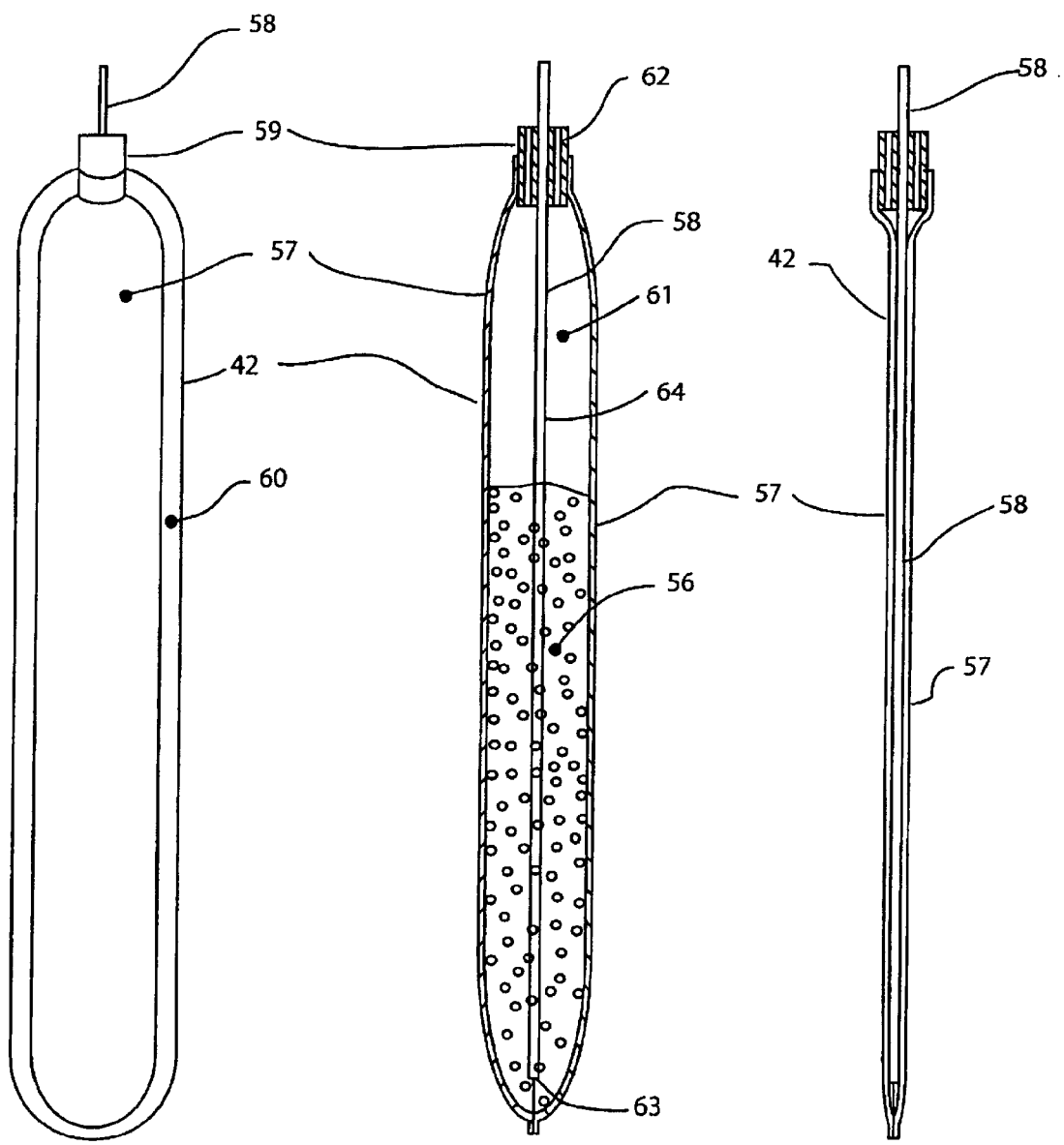
FIG. 8A illustrates a front view of the liquid evaporator assembly of claim 6, according to one embodiment of the invention.
FIG. 8B illustrates, in transverse cross sectional view, an arrangement of the liquid evaporator assembly of FIG. 8A during liquid evaporation.
FIG. 8C depicts, in transverse cross sectional view, an arrangement of the liquid evaporator assembly of FIG. 8A in a storage configuration.

The user control and display interface (not shown) provides allows the user to set operational parameters including set point temperature (temperature to which the patient's body temperature is to be lowered to and then maintained at), and to view operation parameters including actual patient body temperature, and to activate and deactivate patient cooling. Internal container of liquid refrigerant (not shown) is connected to electrically actuated control valve by liquid conduit 11 and connectors 15 & 18. The container of liquid refrigerant may be permanently installed within resuscitation console 7 and be re-filled upon exhaustion, or replaceable after exhaustion. Temperature sensor 19 is connected to electronic control circuits (not shown) by catheter/electrical lead 20 and connectors 14 & 21. Electrically actuated control valve 13 is connected to electronic control circuits (not shown) by electrical conduit 12, and by connectors 15 & 18. Cap assembly 17 (see FIGS. 5, 6, & 9 for construction details) includes electrically actuated control valve 13, at least one evaporator assembly (not shown—see FIG. 8A–8C for construction details), inner wall and outer wall, and space between inner wall and outer wall containing convective heat transfer liquid (not shown—see FIG. 9 for construction details), chinstrap 6, and optionally outer liner or helmet (not shown). Electrically actuated control valve includes a liquid inlet flow control valve (not shown) and an electrical motor (not shown) that actuates the liquid inlet control valve to regulate inlet flow of liquid refrigerant, a gas outlet port and gas outlet pressure regulator (not shown) that allows evaporated refrigerant to be vented to the atmosphere, or scavenged by a gas scavenger (not shown) under a constant predetermined pressure, and a conduit or connector to communicate liquid refrigerant from console 7 into liquid evaporator(s) within cap assembly 17, and a conduit to communicate evaporated refrigerant to gas outlet port and outlet pressure regulator (not shown), and optionally a temperature sensor and a electrical circuit (not shown) that measures the temperature of the evaporated refrigerant as it leaves the cap assembly 7 as an indication of cooling rate, where the flow rate of liquid refrigerant into cap assembly is adjusted by the liquid inlet flow control valve, motor, and electrical circuit according to predetermined algorithms and signals received by the temperature sensor.

The apparatus is used for resuscitation in the following manner: 1.) The cooling cap 8, temperature sensor assembly 9, and resuscitation console 7 is hand carrier to a stricken patient. 2.) The cooling cap assembly 8 is placed onto the patient's head and secured with chinstrap 6. 3.) Temperature sensor 19 is placed on or into the patient's body. 4.) Temperature sensor assembly 9 is connected to console 7 by connector 14 & 21. 5.) Cooling cap assembly 8 is connected to console 7 by connectors 15 & 18. 6.) The user selects operational parameters and then activates the system using the user control and display interface (not shown). 7.) Upon activation of the system, passively pressurized liquid refrigerant flows from the liquid refrigerant container within console 7 into cooling cap assembly 8. Liquid refrigerant is evaporated within the walls of cooling cap 8 into a gaseous state, and absorbs heat from the patient's body as a result of said evaporation. Flow of refrigerant is continuously maintained until either the user deactivates the system, or the patient's body temperature is lowered to the body set point temperature, at which time the system enters a temperature maintenance phase of operation. During the temperature maintenance phase, liquid refrigerant flow into cooling cap assembly is modulated by the control circuit (not shown), of the control console for example, and the electrically actuated control valve assembly 13 according to signals received from temperature sensor 19 to adjust cooling of the patient to maintain patient body temperature at said set point. The system is deactivated upon completion of hypothermia therapy.

Figure 3:
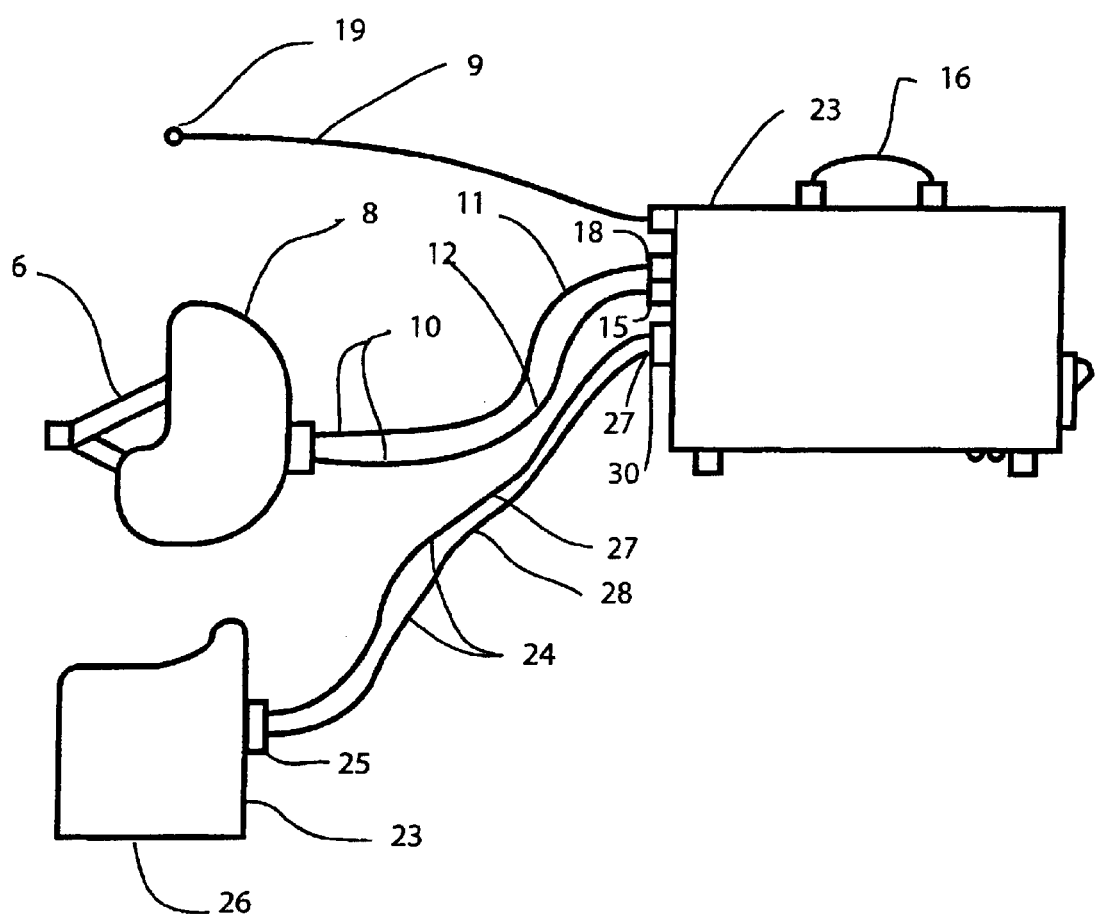
FIG. 3 illustrates the resuscitation apparatus of FIG. 2 having a second body-cooling garment.

FIG. 3 depicts another arrangement of a resuscitation apparatus having small resuscitation console 22, resuscitation-cooling cap 8, temperature sensor assembly 9, umbilical 10, a second cooling-garment 23 (a cooling collar as depicted), and second cooling-garment umbilical 24. Resuscitation-cooling cap 8, temperature sensor assembly 9, and umbilical 10 are described above in the description of FIG. 2. Resuscitation console 22 is as described above in FIG. 2 with the addition of a controller to provide refrigeration liquid to and to control operation of second cooling-garment 23. Second cooling-garment is similar to resuscitation cooling cap 8 in construction and operation and includes umbilical 24, electrically actuated control valve assembly 25, and garment assembly 26. Second cooling garment assembly includes electrically actuated control valve 25, at least one evaporator assembly (not shown—see FIG. 8A–8C for construction details), inner wall and outer wall, and space between inner wall and outer wall containing convective heat transfer liquid (not shown—see FIG. 9 for representative construction details). The operation and construction of electrically actuated control valve assembly 25 is equivalent to electrically actuated control valve assembly 13 in FIG. 2. Second cooling garment may be configured as a collar as depicted, but may also be configured as a vest, trouser, blanket, or any other garment configuration. In one arrangement, when configured as a collar, the cooling garment is configured to cover or contact a shoulder area of a patient, such as the clavicle or axilla area of a patient. Second garment umbilical 24 is equivalent to umbilical 10 of FIG. 2 and includes liquid conduit 27, electrical conduit 28, and console connector 29. Resuscitation console 23 is equivalent to resuscitation console 7 in FIG. 2 with the additional capability of operating two cooling devices concurrently or separately. Resuscitation console 23 has additional umbilical connector 30 for connecting and operating a second cooling-garment. The resuscitation console may be constructed to operated resuscitation cooling-cap 8 or a second cooling-garment 23 simultaneously or independently, or may be constructed to operate two cooling garments where neither cooling garment is a cooling-cap.

The user control and display interface (not shown) of resuscitation console 23 may provide a controller to set operating parameters for each cooling device independently.

Figure 4:
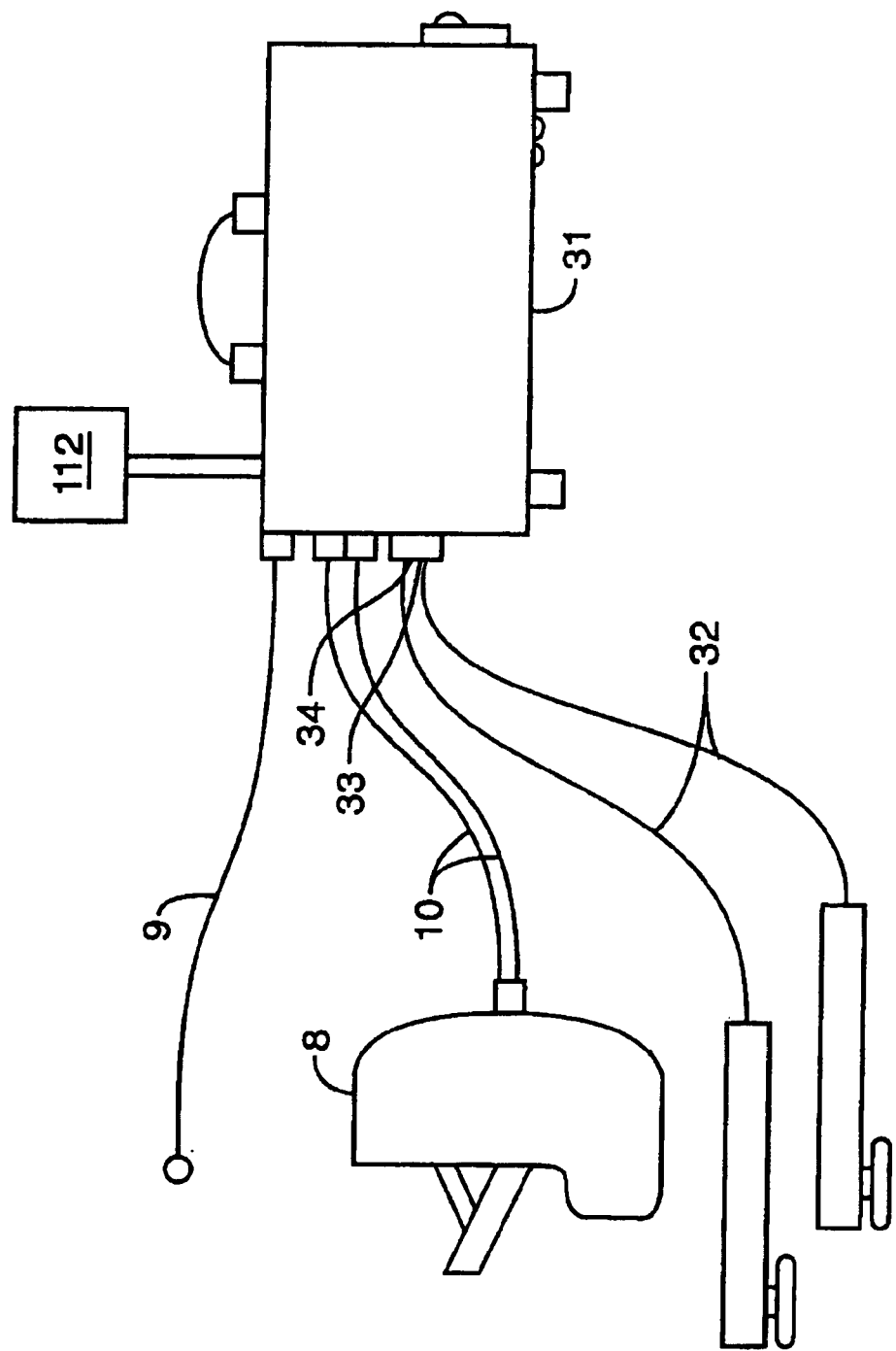
FIG. 4 illustrates the resuscitation apparatus of FIG. 2 having a defibrillator device.

FIG. 4 depicts an arrangement of a resuscitation apparatus having a treatment device, such as a defibrillation apparatus to defibrillate a patient and a hypothermia apparatus to induce hypothermia in a patient, including a small portable resuscitation console 31, resuscitation-cooling cap 8, temperature sensor assembly 9, and defibrillation electrode handles 32. In another arrangement, the resuscitation apparatus includes a treatment apparatus 112, such as a chest compression apparatus, or an intravenous fluid infusion device. For example, in a case where a worker suffers heat exhaustion and is dehydrated, the worker can suffer a cardiac arrest. In such a case the chest compression apparatus and intravenous fluid infusion device of the resuscitation apparatus can be used to resuscitate the patient. Resuscitation console 31 is equivalent to resuscitation console 7 in FIG. 2 with the addition of components for defibrillation, a larger battery sufficient to provide both cooling and defibrillation, a defibrillator electrode paddle connector 33, and the user control and display interface (not shown) may be configured to include controls and display for defibrillation. Defibrillation, both manual and automated is thoroughly disclosed in the art, and requires no further teaching. Defibrillator electrode paddles 33 are of standard configuration for defibrillator electrode paddles and connect to console 31 by console connector 34. Resuscitation cooling cap 8, and temperature sensor assembly 9 as described in FIG. 2. The apparatus is used to resuscitate a patient stricken with cardiac arrest in the following manner: 1.) The cooling cap 8, temperature sensor assembly 9, and resuscitation console 31, and defibrillation electrode paddles 32 are hand carrier to a patient stricken with cardiac arrest. 2.) The patient is then defibrillated using a defibrillator within console 31 and defibrillation electrode paddles 32. 3.) The cooling cap assembly 8 is then placed onto the patient's head and secured with chinstrap 6. 4.) Temperature sensor 19 is placed on or into the patient's body. 5.) Temperature sensor assembly 9 is connected to console 7 by connector means 14 & 21. 6.) Cooling cap assembly 8 is connected to console 7 by connector 15 & 18. 7.) The user selects cooling operational parameters and then activates the system using the user control and display interface (not shown). Cooling is as described above in FIG. 2.

Figure 5:
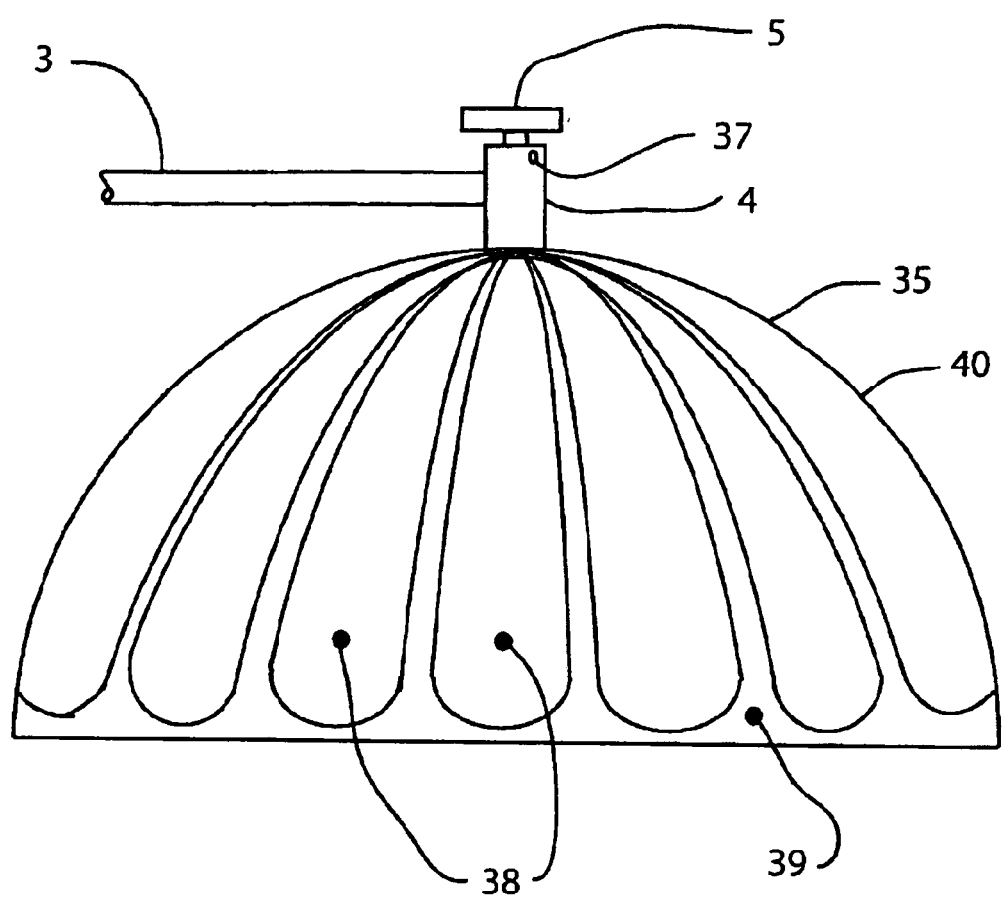
FIG. 5 illustrates an arrangement of the cooling cap or cooling helmet liner of FIG. 1.

FIG. 5 depicts cooling-cap inner liner or helmet cooling-liner assembly 35 with manual control valve assembly 4 including cooling control knob 5, umbilical 3 and gas outlet port 37. Outer liner (not shown) includes insulative foam, or a helmet with a foam insulated inner wall. Finger shaped structures (e.g., chambers) 38 depict convective liquid filled space between inner wall (not shown) and outer wall 40 of cooling cap inner liner assembly 35. Bond area 39 depicts where the inner wall (not shown) outer wall 40 is bonded together to form said convective liquid filled space. Cooling cap inner liner is sized and shaped to cover the cranium of a worker and a patient, and functions to remove heat from a worker to provide comfort, or remove heat from a patient to provide hypothermia therapy. Further construction details and embodiments of cooling-cap inner liner assembly 35 are described below.

Figure 6:
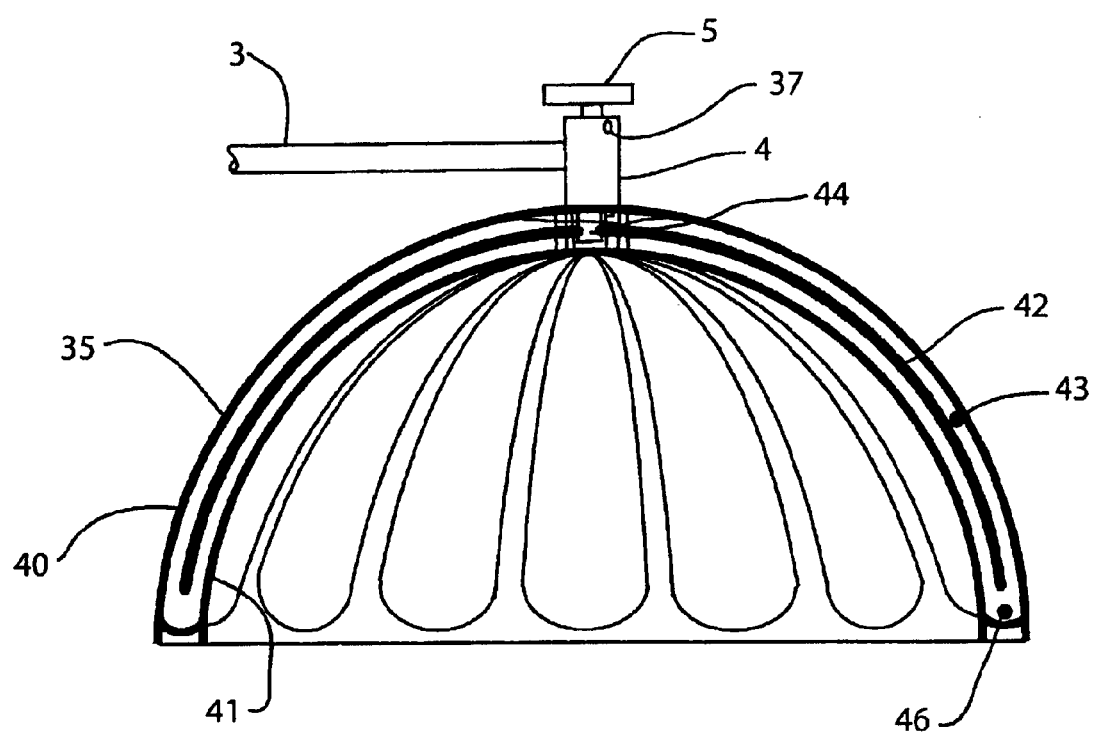
FIG. 6 depicts, in cross sectional view, an arrangement of the functional components and operation of the cooling cap of FIG. 5.

FIG. 6 depicts in cross sectional view cooling cap inner liner assembly 35. Depicted is manual flow control valve 4, umbilical 3, cooling control knob 5, a first or outer wall 40, a second or inner wall 41, evaporator manifold 44, convective heat transfer liquid space 43 having evaporator assembly(s) 42, and convective heat transfer liquid 46.

Cooling cap inner liner assembly 35 removes heat from a worker or a patient in the following manner: 1.) Liquid refrigerant enters control valve assembly 4 through umbilical 3. 2.) The liquid refrigerant flows through control valve assembly 4 into evaporator manifold 44 at a rate that is adjustable by cooling control knob 5. 3.) Evaporator manifold 44 distributes liquid refrigerant into one or more evaporator assemblies 42 (as shown). 4.) The liquid refrigerant enters evaporator assemblies 42 and evaporates due to heat absorption from surrounding convective heat transfer liquid 46 through the walls of evaporator assembly 42. 5.) As heat is absorbed from surrounding convective heat transfer liquid 46 the temperature of the heat transfer liquid 46 is lowered to a temperature lower than the body temperature of the worker or the patient, thereby causing heat to be transferred from the worker's or patient's head into the convective heat transfer liquid though inner wall 41 which, thereby results in a heat flux between the head of the worker or the patient and the liquid refrigerant causing evaporation of the liquid refrigerant. The heat transfer fluid 46 acts to substantially evenly distribute cooling, as provided by the evaporation of the liquid refrigerant, to the head of the worker (e.g., the portion contacting the cooling garment) to minimize localized "cold spots" within the chamber. 6.) Evaporated refrigerant is vented into the atmosphere thought evaporator manifold 44, control valve assembly 4, and gas outlet port (e.g., vent) 37. Convective heat transfer liquid 46 may include water, or some other liquid. Convective heat transfer liquid 46 may include water and an anti-freeze agent such as ethylene glycol and be formulated such that convective heat transfer liquid 46 freezes at a temperature below zero degrees centigrade whereby the temperature of convective heat transfer liquid 46 will not drop below said freezing point while said convective heat transfer liquid 46 is at least in part in a liquid state. The heat transfer fluid, in turn, reduces the temperature of the body portion in thermal communication with the cooling garment.

The freezing point of convective heat transfer liquid 46 in one arrangement is formulated such that the surface of inner wall 41 in contact with the worker's or patient's skin is just above zero degrees centigrade. With the surface of inner wall 41 in contact with the worker's or patient's skin at just above zero degrees centigrade, heat transfer will be at a maximal level possible while minimizing frostbite injury to the worker's or patient's skin. The flow rate of the liquid refrigerant may be limited by the design and construction of control valve assembly 4 such that freezing of all of the convective heat transfer liquid 46 will not be possible during normal use.

Figure 7:
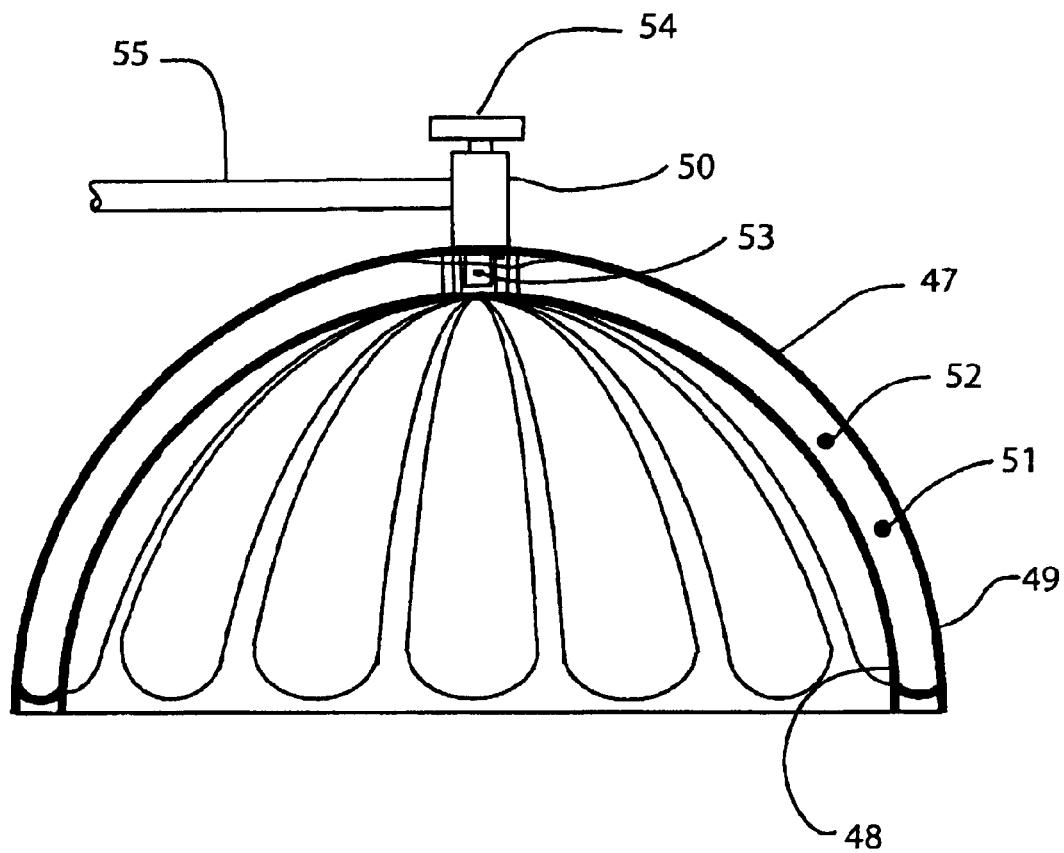
FIG. 7 depicts, in cross sectional view, an arrangement of the functional components and operation of the cooling cap of FIG. 5.

FIG. 7 depicts an alternate embodiment of the cooling-cap inner liner assembly whereby an evaporator assembly is not required. Inner cooling-cap liner assembly 47 includes inner wall 48, outer wall 49, convective heat transfer liquid space 51 formed between inner wall 48 and outer wall 49, convective heat transfer liquid 52, and control valve assembly 50 having cooling control knob 54, umbilical 55, and liquid refrigerant port 53. Inner wall 48 is constructed from a polymer such as polyethylene. Outer wall 49 is constructed from a gas permeable membrane such as Tyvek.® During operation, liquid refrigerant flows into control valve assembly 50 from umbilical 55, and into convective heat transfer liquid space 51 containing convective heat transfer liquid 52 through liquid refrigerant port 53. Liquid refrigerant is evaporated by direct contact with, and heat absorption from convective heat transfer liquid 52. Direct evaporation of liquid refrigerant within convective heat transfer liquid 52 causes a boiling like effect and enhanced convection within convective heat transfer liquid space 51. Gas resulting from evaporation of liquid refrigerant is vented into the atmosphere though outer wall 49 where the outer wall is formed of a gas permeable membrane. In such an arrangement, the gas permeable membrane acts as vent for the cooling assembly.

FIG. 8A–C depicts evaporator assembly 42. FIG. 8A depicts the front view of evaporator assembly 42. FIG. 8B depicts a transverse sectional side view of evaporator assembly 42 during operation depicting the evaporation process of liquid refrigerant 56. FIG. 8C depicts a transverse sectional view of evaporator 42 in a pre-use or storage configuration. Evaporator assembly 42 includes walls 57 fabricated from a metal foil such as aluminum or titanium and are welded together at weld seam 60; liquid feed tube 58 having a flexible polymer or metallic tube with an inside diameter of 0.5 to 1.5 mm, and a manifold ferrule 59. Ferrule tube 59 includes gas port 62. Liquid refrigerant 56 enters evaporator assembly 42 through liquid feed tube 58. Evaporated refrigerant leaves evaporator assembly 42 through gas port 62. Prior to use, or after use evaporator assembly may be folded into a compact shape as depicted in FIG. 8C. Manifold ferrule may be machined out the same material as evaporator assembly walls 57 and welded into place as shown. Liquid feed tube 58 may be held in place with an adhesive, or if metallic, welded in place as shown. Distal end 63 of liquid feed tube 58 may have an open end as shown, where liquid refrigerant 56 enters evaporator assembly through distal end 63. Alternatively, liquid feed tube 58 may be configured with distal end 63 closed and liquid feed tube wall 64 includes a series of small hoes between 0.05 and 0.15 mm in diameter where liquid refrigerant 56 enters evaporator assembly 42 through said holes.

Figure 9:
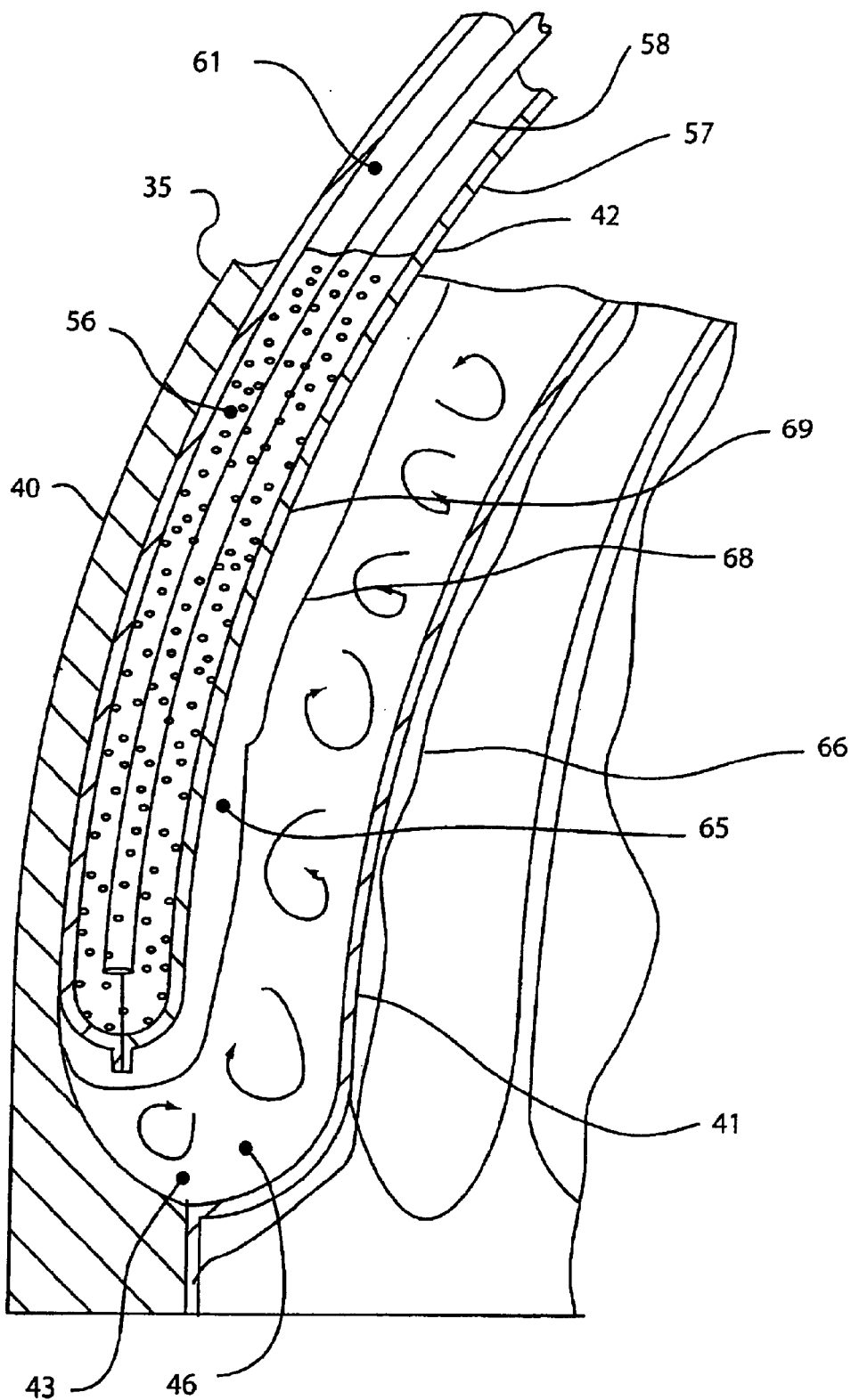
FIG. 9 depicts, in cross sectional view, the operation of the cooling mechanism of the cooling cap or cooling helmet liner showing the inner wall, the outer wall, the liquid evaporator, and the convective heat transfer liquid space between the inner wall, and the outer wall.
Figure 10:
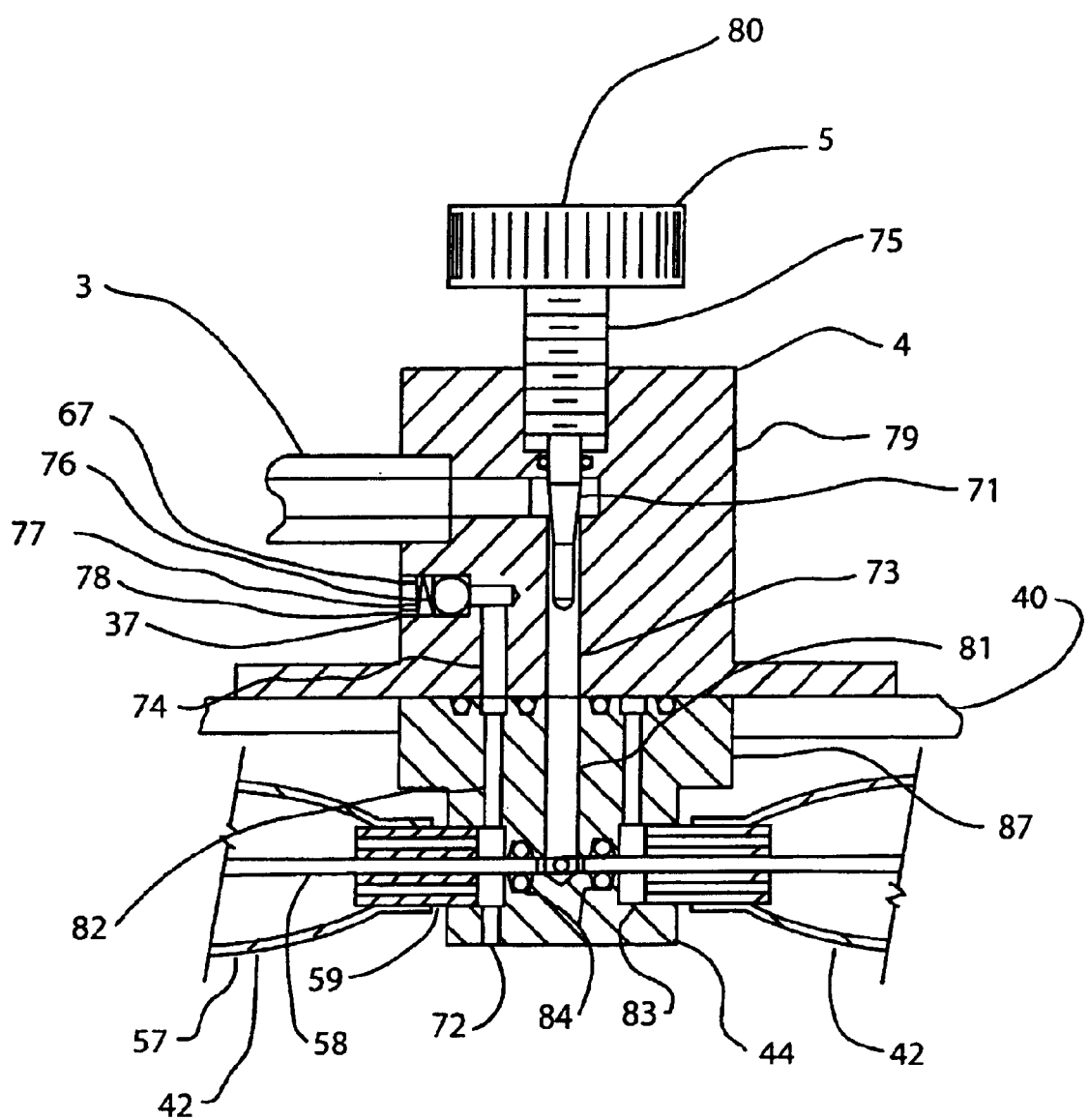
FIG. 10 depicts, in cross sectional view, the manual control valve assembly of the cooling-cap, or the cooling helmet liner.

FIG. 9 depicts in cross sectional view the operation of the cooling mechanism of cooling cap 8 (or cooling helmet liner) showing inner cooling-cap liner assembly 35, inner wall 41, outer wall 40, evaporator assembly 42, convective heat transfer liquid space 43, convective heat transfer liquid 46, liquid refrigerant 56, evaporated refrigerant 61, ice formation 65, and heat transfer liquid or gel 66. Liquid refrigerant 56 boils at a cryogenic temperature determined by the physical properties of the refrigerant, and the pressure within evaporator assembly 42. The pressure within evaporator assembly 42 is controlled by pressure relief valve 67 of control valve assembly 4 at a value between 1 and 40 PSIG (FIG. 10). At an operating pressure between 1 and 40 PSIG, liquid nitrogen will boil (or evaporate) at a temperature near minus 190 degrees centigrade. Convective heat transfer liquid 46 includes water and an antifreeze agent and is formulated to have a freezing point between zero and minus thirty degrees centigrade. Due to the cryogenic temperature generated by said boiling within evaporator assembly 42, outer surface 69 of evaporator assembly 42 will also be at a cryogenic temperature. Ice formation 65 develops at outer surface 70 of evaporator assembly 42 as shown. The temperature at outer layer 68 of ice formation 65 is very near the freezing point of convective heat transfer liquid 46. The temperature at inner layer 69 of ice formation 65 is very near the temperature of outer wall 70 of evaporator assembly 42. Heat transfer liquid or gel 66 is placed into the hair of the worker or patient, or is placed onto inner wall 41 prior to placing cooling-cap 8 onto the head as shown. Heat transfer liquid or gel 66 provides a heat transfer medium between the worker's or the patient's scalp, for example, and inner wall 41, and greatly diminishes the insulating effect of hair. Arrows indicate convective heat transfer between inner wall 41 and ice formation 65 and evaporator assembly 42.

FIG. 10 depicts in sectional view control valve assembly 4, evaporator manifold assembly 44, evaporator assemblies 42, and outer wall 40 of cooling-cap inner liner assembly 35. Control valve assembly 4 includes valve housing 79, needle valve assembly 80, umbilical 3, liquid passage 73, gas passage 74 and pressure relief valve assembly 67. Evaporator manifold assembly 44 includes manifold housing 87, gas passage 82, evaporator receptacles 83, liquid feed tube o-rings 84, inner gas passage o-ring 85, and outer gas pressure o-ring 86. Evaporator assemblies 42 (see FIG. 8) include evaporator walls 57, liquid feed tube 58, and manifold ferrule 59. Needle valve assembly 80 includes needle valve 71, needle valve adjustment screw 75, and cooling control knob 5. Pressure relief valve assembly 67 includes ball 76, spring 77, and spring ferrule 78. Valve housing 79, manifold housing 87, needle valve 71, and needle valve adjustment screw 75 may be machined from stainless steel as shown. Pressurized liquid refrigerant 56 enters control valve assembly though umbilical 3. Needle valve 71 controls the flow rate of liquid refrigerant 56 into liquid passage 73. Control knob 5, and needle valve adjustment screw 75 control the position of needle valve 71 whereby, movement of needle valve 71 down reduces the flow rate of liquid refrigerant 56, and movement of needle valve 71 up increases the flow rate of liquid refrigerant 56. Liquid refrigerant flows through liquid passages 73 and 81 and into liquid feed tube 58 of liquid evaporator assemblies 42 as shown. Liquid feed tube o-rings 84 isolate liquid passage 81 from gas passage 82. Evaporated refrigerant 61 leaves evaporator assembly 42 through gas passage 82 and 74, and exits control valve assembly through pressure relief valve assembly 67 as shown. Gas pressurization port 72 allows pressurization of convective heat transfer liquid space at the pressure of the evaporator operating pressure to provide inward expansion of inner wall 41 (FIG. 9) and a snug fit of cooling cap 8 with the head which provides enhanced heat transfer between the head and inner wall 41. Evaporator assemblies 42 may be welded to evaporator manifold housing 87 as shown, or may be fastened by some other fastener. Manifold housing 87 may be bolted to valve housing 79. Inner o-ring 85, and outer o-ring 86 provide isolation of liquid passages 73 and 81, from gas passages 74 and 82, and from the atmosphere. Outer wall 40 may be bonded or fastened to valve housing 79 by a fastener appropriate based of specific material considerations.

While this invention has been particularly shown and described with references to embodiments thereof, it will be understood by those skilled in the art that various changes in form and details may be made therein without departing from the spirit and scope of the invention as defined by the appended claims.

The body temperature sensor may be in the form of a Foley catheter, or an esophageal catheter, or a rectal probe, or a tympanic temperature sensor, or a scalp temperature sensor.

The liquid flow control valve may be constructed to automatically control liquid refrigerant flow into the cooling helmet using valves similar to thermostatic expansion valves used in commercial refrigeration systems.

Returning to FIG. 1, in one arrangement, the cooling-cap or garment includes an iontophoresis assembly 90 that delivers a medication to a patient. During the process of iontophoresis, electric current passes through a solution containing ions, usually the ionic form of a drug or therapeutic agent. The current forces the medication to enter the patient's bloodstream through the skin.

As illustrated in FIG. 1, for example, the cooling garment 2 includes the iontophoresis assembly 90 that includes an anode 92, a cathode 94, and a power source 96 to provide a direct current voltage to the anode 92 and cathode 94. In one arrangement, the iontophoresis assembly 90 delivers a anesthetic agent, such as a topical contained within gel 66, as illustrated in FIG. 9, to minimize cold sensation in the scalp during operation of the cooling assembly.

The heat transfer liquid or gel may include a suspension of metal powder to enhance heat transfer from the head to the inner wall, or a topical anesthetic to minimize cold sensation in the scalp.

Professional or amateur athletes may use embodiments of the invention during an athletic event for comfort or to prevent or recover from heat exhaustion.

A means other than convective heat transfer liquid may be used to transfer heat from the inner wall to the evaporator assembly.

The cooling source may be mounted in a vehicle. The cooling source may also be a refrigeration system mounted in a vehicle.

The liquid flow control valve may be located at the cooling source.

What is claimed is:

1. A cooling assembly comprising:
 a cooling garment configured to thermally contact a body portion, the cooling garment having a first wall and a second wall defining a chamber;
 a fluid inlet coupled to the cooling garment, the fluid inlet configured to couple to a pressurized liquid refrigerant source and deliver a liquid refrigerant from the pressurized liquid refrigerant source to the chamber;
 a vent coupled to the cooling garment and in fluid communication with the chamber, the vent configured to allow release of evaporated liquid refrigerant from the chamber as the liquid refrigerant evaporates within the chamber; and
 a heat transfer fluid within the chamber and in thermal communication with the liquid refrigerant, the heat transfer fluid configured to exchange heat between the liquid refrigerant and the body portion in thermal contact with the cooling garment as the liquid refrigerant evaporates within the chamber.

2. The cooling assembly of claim 1 wherein the cooling garment comprises an evaporator assembly in fluid communication with the heat transfer fluid, the evaporator assembly configured to receive the liquid refrigerant from the pressurized liquid refrigerant source via the fluid inlet.

3. The cooling assembly of claim 2 wherein the evaporator assembly comprises a pressure relief valve configured to maintain a pressure within the evaporator chamber and control evaporation of the liquid refrigerant.

4. The cooling assembly of claim 1 wherein the fluid inlet comprises a flow control valve.

5. The cooling assembly of claim 1 wherein the cooling garment is chosen from the group consisting of a cap, a vest, trousers, a blanket, or a collar.

6. The cooling assembly of claim 1 wherein the vent comprises a gas permeable membrane forming at least one of the first wall and the second wall of the cooling garment.

7. The cooling assembly of claim 1 wherein the cooling garment comprises an iontophoresis assembly.

8. A cooling system comprising:
 a pressurized liquid refrigerant source having a liquid refrigerant; and
 a cooling assembly having:
  a cooling garment configured to thermally contact a body portion, the cooling garment having a first wall and a second wall defining a chamber;

a fluid inlet coupled to the cooling garment, the fluid inlet coupled to the pressurized liquid refrigerant source and configured to deliver the liquid refrigerant from the pressurized liquid refrigerant source to the chamber;

a vent coupled to the cooling garment and in fluid communication with the chamber, the vent configured to allow release of evaporated liquid refrigerant from the chamber as the liquid refrigerant evaporates within the chamber; and a heat transfer fluid within the chamber and in thermal communication with the liquid refrigerant, the heat transfer fluid configured to exchange heat between the liquid refrigerant and the body portion in thermal contact with the cooling garment as the liquid refrigerant evaporates within the chamber.

9. The cooling system of claim 8 wherein the cooling garment comprises an evaporator assembly in fluid communication with the heat transfer fluid, the evaporator assembly configured to receive the liquid refrigerant from the pressurized liquid refrigerant source via the fluid inlet.

10. The cooling system of claim 9 wherein the evaporator assembly comprises a pressure relief valve configured to maintain a pressure within the evaporator chamber and control evaporation of the liquid refrigerant.

11. The cooling system of claim 8 wherein the fluid inlet comprises a flow control valve.

12. The cooling system of claim 8 wherein the cooling garment is chosen from the group consisting of a cap, a vest, trousers, a blanket, or a collar.

13. The cooling system of claim 8 wherein the vent comprises a gas permeable membrane forming at least one of the first wall and the second wall of the cooling garment.

14. The cooling system of claim 8 wherein the cooling garment comprises an iontophoresis assembly.

15. The cooling system of claim 8 further comprising a gel in thermal communication with the cooling garment and configured to thermally contact the body portion.

16. The cooling system of claim 15 wherein the gel comprises an anesthetic agent.

17. The cooling system of claim 11 further comprising a control console having a physiological sensor configured to contact a subject, the control console coupled to the flow control valve and configured to receive a signal from the physiological sensor and adjust the flow control valve to adjust cooling of the subject based upon the received signal.

18. A method for altering a temperature of a subject comprising:

thermally contacting a cooling garment with a body portion of the subject, the cooling garment having a first wall and a second wall defining a chamber, a fluid inlet coupled to the cooling garment, a vent coupled to the cooling garment and in fluid communication with the chamber, and a heat transfer fluid within the chamber;

coupling the fluid inlet to a pressurized liquid refrigerant source; and activating the pressurized liquid refrigerant source to deliver a liquid refrigerant from the pressurized liquid refrigerant source to the chamber, the heat transfer fluid configured exchanging heat between the liquid refrigerant and the body portion in thermal contact with the cooling garment as the liquid refrigerant evaporates within the chamber and the vent allowing release of evaporated liquid refrigerant from the chamber as the liquid refrigerant evaporates within the chamber.

19. The method of claim 18 comprising:

applying a heat transfer gel to the body portion of the subject; and placing the cooling garment in thermal communication with the gel.

20. The method of claim 18 comprising:

coupling a physiological sensor with the subject;

coupling a control console to a flow control valve associated with the fluid inlet of the cooling garment; and activating the control console to (i) receive a signal from the physiological sensor and (ii) adjust the flow control valve in response to the signal received from the physiological sensor to adjust cooling of the subject.

21. The cooling system of claim 8 further comprising:

a housing coupled to the pressurized liquid refrigerant source; and a treatment device coupled to the housing, the treatment device chosen from the group consisting of a defibrillation device, a chest compression apparatus, or an intravenous fluid infusion device.

* * * * *